(12) United States Patent
Cai et al.

(10) Patent No.: US 8,075,895 B2
(45) Date of Patent: Dec. 13, 2011

(54) IDENTIFICATION OF ANTIGENIC PEPTIDES FROM MULTIPLE MYELOMA CELLS

(75) Inventors: Zeling Cai, San Diego, CA (US);
Wei-Xing Shi, San Diego, CA (US);
Xuejun P. Liu, San Diego, CA (US);
Jiejun Wu, San Diego, CA (US)

(73) Assignee: Janssen Pharmaceutica N.V., Beerse (BE)

( * ) Notice: Subject to any disclaimer, the term of this patent is extended or adjusted under 35 U.S.C. 154(b) by 99 days.

(21) Appl. No.: 12/564,501

(22) Filed: Sep. 22, 2009

(65) Prior Publication Data

US 2011/0070185 A1  Mar. 24, 2011

(51) Int. Cl.
*A61K 39/00* (2006.01)
*C07K 14/00* (2006.01)

(52) U.S. Cl. .................................. 424/184.1; 530/300

(58) Field of Classification Search .................. None
See application file for complete search history.

(56) References Cited

U.S. PATENT DOCUMENTS

| | | | |
|---|---|---|---|
| 4,690,915 | A | 9/1987 | Rosenberg |
| 4,844,893 | A | 7/1989 | Honsik et al. |
| 5,126,132 | A | 6/1992 | Rosenberg |
| 5,443,983 | A | 8/1995 | Ochoa et al. |
| 5,766,920 | A | 6/1998 | Babbitt |
| 5,846,827 | A | 12/1998 | Celis et al. |
| 6,040,177 | A | 3/2000 | Riddell et al. |
| 6,194,207 | B1 | 2/2001 | Bell |
| 6,225,042 | B1 | 5/2001 | Cai et al. |
| 6,251,385 | B1 | 6/2001 | Terman |
| 6,255,073 | B1 | 7/2001 | Cai et al. |
| 6,355,479 | B1 | 3/2002 | Webb et al. |
| 6,362,001 | B1 | 3/2002 | Cai et al. |
| 6,790,662 | B1 | 9/2004 | Leturcq |
| 7,402,314 | B2 | 7/2008 | Sherman |
| 2002/0119121 | A1 | 8/2002 | Vitiello et al. |
| 2007/0258959 | A1 | 11/2007 | Schuler et al. |
| 2009/0004142 | A1 | 1/2009 | Leturcq et al. |
| 2009/0010950 | A1 | 1/2009 | Roncarolo et al. |
| 2009/0017000 | A1 | 1/2009 | Cai et al. |

FOREIGN PATENT DOCUMENTS

| | | |
|---|---|---|
| WO | WO 02/22648 | 3/2002 |
| WO | WO 2007/103009 | 9/2007 |

OTHER PUBLICATIONS

Andersen et al., *Tissue Antigens.* 54(2):185-90 (1999).
Baccala et al., *J. Immunol.*, vol. 174, pp. 4606-4612 (2005).
Brunner et al., *Immunology.* 14(2):181-96 (1968).
Carter et al., *Curr. Opin. Immunol.*, vol. 8(3), pp. 336-342 (1996).
Cerwenka et al., *J. Immunol.*, vol. 163(10), pp. 5535-5543 (1999).
Cerwenka et al., *J. Immunol.*, vol. 161, pp. 97-105 (1998).
Croft et al., *J. Exp. Med.*, vol. 180, pp. 1715-1728 (1994).
Dudley ME, et al, *Science.* 298(5594):850-4 (2002).
Fujihashi et al., Proc. Natl. Acad. Sci. USA, vol. 93, pp. 3613-3618 (1996).
Goldrath et al., *J. Exp. Med.*, vol. 192, pp. 557-564 (2000).
Ishimaru et al., *Nature Immunol.*, vol. 7(7), pp. 763-772 (2006).
Kaech et al., *Cell*, vol. 111, pp. 837-851 (2002).
Kern et al., *Eur. J. Immunol.*, vol. 29, pp. 2908-2915 (1999).
Kieper et al., *J. Immunol.*, vol. 174, pp. 3158-3163 (2005).
Kieper et al., *Proc. Natl. Acad. Sci. USA*, vol. 96, pp. 13306-13311 (1999).
Kyle RA and Rajkumar SV. , *N. Engl J Med.*351(18):1860-73 (2004).
Livingston et al., Immunol. Invest., vol. 24(4), pp. 619-629 (1995).
Lu et al., *Cancer Immunol Immunother.* 58(4):629-38 (2009).
McFarland et al., *PNAS*, vol. 97(8), pp. 4215-4220 (2000).
Mosmann et al., *Immunol. Today*, vol. 17(3), pp. 138-146 (1996).
Münz et al., *J Immunol.* 162(1):25-34 (1999).
Murali-Krishna et al., *J. Immunol.*, vol. 165, pp. 1733-1737 (2000).
Opferman et al., *Science*, vol. 283, pp. 1745-1748 (1999).
Parham and Brodsky, *Hum Immunol.* 3(4):277-99 (1981).
Parker et al., *J Immunol.*149(11):3580-7 (1992).
Parkhurst MR, et al, *J Immunol.*157(6):2539-48 (1996).
Rosenberg SA, et al, *Nat Med.*4(3):321-7 (1998).
Sad et al., *Immunity*, vol. 2, pp. 271-279 (1995).
Sadovnikova et al., *Eur J Immunol.* 28(1):193-200 (1998).
Schneider, *J. Embryol. Exp. Morph.* vol. 27, pp. 353-365 (1972).
Townsend et al., *Cell.*62(2):285-95 (1990).
Walzer et al., *Cell. Immunol.*, vol. 206, pp. 16-25 (2000).
Wherry et al., *Nat. Immunol.*, vol. 4, pp. 225-234 (2003).
Yee C, et al, *Proc Natl Acad Sci U S A.* 99(25):16168-73 (2002).
Zhang et al. *Immunology.* 121(1):105-12 (2007).

*Primary Examiner* — Michail Belyavskyi

(57) ABSTRACT

Multiple myeloma (MM) is a clonal B cell malignancy and remains essentially incurable by conventional anti-tumor therapy. Patients with MM have a median survival of only three years. MM is characterized by proliferation and accumulation of mature plasma cells in the bone marrow (BM) leading to bone destruction, BM failure, anemia, and reduced immune function. The identification of MHC Class I, HLA-A2, associated peptides presented on multiple myeloma cells is an important step in developing immunotherapies for MM. Presented here are methods for creating activated T lymphocytes that are cytotoxic to both peptide loaded T2 target cells and multiple myeloma cell lines.

3 Claims, 19 Drawing Sheets

IDENTIFICATION OF ANTIGENIC PEPTIDES FROM MULTIPLE MYELOMA CELLS

TECHNICAL FIELD

The present invention generally relates to biology, immunology, and novel antigenic peptides. More particularly the present invention relates to antigenic peptides identified from multiple myeloma cell lines that reproducibly produce activated T lymphocytes that are cytotoxic to peptide-loaded target cells and multiple myeloma cells. The invention further relates to the use of the activated T lymphocytes as antigen-specific cytotoxic T lymphocytes (CTL) in the treatment of multiple myeloma.

BACKGROUND OF THE INVENTION

Various publications, which may include patents, published applications, technical articles and scholarly articles, are cited throughout the specification in parentheses, and full citations of each may be found at the end of the specification. Each of these cited publications is incorporated by reference herein, in its entirety.

Cytotoxic T lymphocytes (CTL) play an important role in the mammalian immune reaction to foreign materials and are capable of inducing the death of tumor cells in vivo. CTL are derived from naïve CD8+ T cells and recognize antigenic peptides presented by Major Histocompatibility Complex (MHC) class I cell surface receptors, also referred to as human leukocyte antigens (HLA). Naïve T cells are distinguished from activated T cells in that they have not yet encountered an antigen or other signal required for activation. It is generally accepted that two signals are required for induction of naïve T cells. Signal 1 is induced by the interaction between the T Cell Receptor (TCR) and the MHC/antigenic peptide complex and is aided by binding of CD8 co-receptors to non-polymorphic regions of MHC class I molecules. Signal 2 is qualitatively different from Signal 1 and is delivered via T cell co-stimulatory molecules interacting with complementary ligands on Antigen Presenting Cells (APC) that express MHC class II and co-stimulatory molecules. Signals 1 and 2 function synergistically and trigger a series of signalling events which ultimately induce T cells to proliferate, produce cytokines, and differentiate into antigen-specific CTL that can then travel throughout the body to search for and destroy other specific antigen-positive cells.

In addition it has been demonstrated that responses to cellular antigens are dependent on help delivered by CD4+ T cells, i.e., Helper T Lymphocytes (HTL). The nature of this help has been interpreted as the need for activated HTL to produce IL-2 necessary for CTL expansion. Recent studies have also shown that this help results from the activation of dendritic cells by HTL and is mediated via the interaction of CD40 and its ligand. Dendritic cells have been shown to be highly potent inducers of CTL responses and are thought to be the principal APC involved in priming CTL. It is generally accepted that APC, through mechanisms unique to these cells, take up antigens either in the form of soluble antigen associated with chaperone molecules or by phagocytosis.

In recent years, many genes encoding tumor associated antigens (TAA) that can be recognized by CTL have been identified from cDNA of a variety of human tumor cells. For example, the identification of TAA in melanoma has led to clinical trials to test therapies that target cancer cells using vaccination strategies in which the antigens are delivered in an immunogenic context in an attempt to induce potent T cell responses in vivo. These vaccination strategies with TAA hold promise for the development of novel cancer immunotherapies.

Adoptive immunotherapy is another strategy that holds promise as a novel cancer immunotherapy. Adoptive immunotherapy involves in vitro activation and expansion of T cells specific for one or more tumor antigens and subsequent treatment of patients with the activated T cells. Compared to vaccination therapies using TAA, adoptive T cell therapy has advantages because it involves the removal of T cells from the host environment where tolerogenic mechanisms can affect the immunogenic response. Furthermore, studies in mouse tumor models have demonstrated that adoptive immunotherapy can be efficacious with minimal toxicity. In the past, one obstacle in applying this strategy to the treatment of human tumors was the lack of information about immunogenic antigens that would render tumor cells susceptible to CTL-mediated destruction. More recently, however, isolation of tumor-reactive T cells from cancer patients has led to the identification of TAA to which CTL are directed. Some of these include tyrosinase, MART-1/Melan A, gp100, and MAGE. Of these, tyrosinase and MART-1 are nearly universally expressed on melanoma cells and therefore represent a desired target choice for adoptive immunotherapy for patients with melanoma.

Early adoptive immunotherapy approaches used Lymphokine-activated killer cells (LAK) and later tumor-infiltrating lymphocytes (TIL), both activated ex vivo with IL-2. The demonstration of efficacy was equivocal, however, and thus these early controlled clinical trials failed to show an advantage to the use of the ex vivo-activated cells over the direct administration of IL-2 to melanoma patients. More recent studies have clearly demonstrated the potential for certain adoptive T-cell therapeutic approaches (Yee et al., *PNAS*, Vol. 99, pp. 16168-16173, (2002); Dudley et al., *Science*, Vol. 298, pp. 850-854, (2002)). These studies involved use of either T-cell clones specific for MART-1 or gp100 and low-dose IL-2, or TILs expanded ex vivo with allogeneic feeder cells and high-dose IL-2. These studies confirmed that adoptive immunotherapy holds promise as a treatment for cancer.

The use of artificial antigen presenting cells (aAPCs) is an ex vivo method to reproducibly generate therapeutic numbers of antigen specific CD8+ T cells. For although it is possible to use naturally occurring APCs for T cell activation in vitro (e.g., dendritic cells, macrophages, B-cells, or autologous tumor cells), the efficiency of activation can be low since the MHC molecules of naturally occurring APCs contain many other peptide epitopes. As a result, there may be minimal presentation of selected epitopes. In addition, most of these presented peptides represent normal, innocuous endogenous proteins. A more direct approach to this problem is to activate CD8+ T cells specifically to only those epitopes relevant to combating the disease. This approach is accessible using aAPCs (See e.g. U.S. Pat. Nos. 6,225,042, 6,355,479, 6,362,001 and 6,790,662; U.S. Patent Application Publication Nos. 2009/0017000 and 2009/0004142; and International Publication No. WO2007/103009).

One such aAPC has been developed utilizing a *Drosophila melanogaster* (fruit fly) embryonic cell line, which expresses the major histocompatibility complex (MHC) Class I molecules. *Drosophila* lacks homologues to human TAP1 and TAP2 peptide transporters, which are involved in the loading of peptide epitopes into the human MHC molecules. As a result, transfected Class I molecules and Class II molecules appear on the *Drosophila* cell surface as empty vessels. By incubating *Drosophila* cells transfected with MHC Class I- or MHC Class II-encoding expression vectors with one or more exogenous synthetic peptides that bind to the specific MHC molecules (i.e., TAA for presentation as T-cell peptide epitopes), all of the available MHC molecules may be occupied with MHC-restricted, specific peptide epitope(s). In particular, the high density expression of HLA-A2.1 MHC Class I molecules presenting single or multiple peptide epitopes, and the addition of key assisting molecules B7-1 (CD80), LFA-3 (CD58), ICAM-1 (CD54), and CD70 on these *Drosophila* aAPCs, permits the in vitro generation of potent, autologous cytotoxic CD8+ T cells which are specific for the selected peptides and suitable for use as a cell therapy.

One such cell therapy comprises an autologous immunotherapeutic product prepared with ex vivo-activated autologous CD8+ CTL exhibiting peptide specificity for selected HLA-A2.1-restricted peptides from melanoma-associated antigens. The active component of the cell therapy product is the patient's own CD8+ cells, which have been activated ex vivo by exposure to selected peptide-loaded aAPCs having specificity for the selected HLA-A2.1 restricted peptides. To generate the cell therapy product, the CTL are: 1) derived from autologous naïve T cells isolated from lymphapheresis samples harvested at a clinical site; 2) primed ex vivo against melanoma antigenic peptide epitopes using *Drosophila* cells as the aAPCs; 3) expanded by restimulation with autologous monocytes loaded with the melanoma antigenic epitopes preferably in the presence of both Interleukin-2 (IL-2) and Interleukin-7 (IL-7), followed by non-specific expansion using OKT®3; 4) harvested, washed, and re-suspended in final formulation for infusion; and, 5) infused into the patient from which the CD8+ cells were derived. The final cell therapy product for re-infusion preferably contains 1-10×10$^9$ CTL cells in 300 mL of Lactated Ringer's Injection Solution (76% v/v), 5% dextrose in normal saline (D5NS) (4% v/v), and human serum albumin (HSA) (20% v/v).

These promising new immunotherapies utilizing specific antigens for ex vivo-activation of autologous CD8+ CTL offer a promising strategy for the treatment of cancer. This is an especially exciting development for cancers that are incurable with current therapies. Multiple myeloma (MM) is a clonal B cell malignancy with an incidence of approximately 15,000 new cases per year in the United States. MM has a median survival of only three years and is characterized by proliferation and accumulation of mature plasma cells (PC) in the bone marrow (BM) leading to bone destruction, BM failure, anemia, and reduced immune function. MM remains essentially incurable by conventional anti-tumor therapy (Kyle and Rajkumar, *N Engl J Med.* 2004 Oct. 28; 351(18): 1860-73. The identification of myeloma-specific antigenic peptides uniquely presented on multiple myeloma cells is an important step in the development of an effective immunotherapy treatment for MM.

SUMMARY OF THE INVENTION

The invention is directed to the embodiments defined herein and by the independent and dependent claims appended hereto. Embodiments, features, and advantages of the various aspects of the invention will become apparent from the detailed description below taken in conjunction with the appended drawing figures.

In one embodiment, the present invention comprises a synthetic peptide that is capable of activating T lymphocytes, wherein the synthetic peptide comprises an amino acid sequence selected from the group consisting of: SLVLNLLEL (SEQ ID NO:3), KNPVLLKIL (SEQ ID NO:7), NLLPKLHVV (SEQ ID NO:9), FLLPHPGLQV (SEQ ID NO:10), LLNMPPAHLK (SEQ ID NO:11), TLVDLPGMTKV (SEQ ID NO:13), TLIDLPGITRV (SEQ ID NO:14), LSLDSSLSSLL (SEQ ID NO:17), LLLDVAYGAVQA (SEQ ID NO:22), FLASESLLKGAL (SEQ ID NO:23), LVLNLLE (SEQ ID NO:32), TLVDLPGM (SEQ ID NO:40), IDLPGITR (SEQ ID NO:61), WLTVLFIFRI (SEQ ID NO:66), LVYLGHVIYL (SEQ ID NO:67), FVPEVSFEL (SEQ ID NO:70), and FQMEQIVYC (SEQ ID NO:72); and wherein the activated T lymphocytes are cytotoxic to multiple myeloma cancer cells.

In a second embodiment, the present invention comprises a composition comprising at least one antigenic peptide that is capable of activating T lymphocytes, wherein the antigenic peptide comprises an amino acid sequence selected from the group consisting of: SLVLNLLEL (SEQ ID NO:3), KNPVLLKIL (SEQ ID NO:7), NLLPKLHVV (SEQ ID NO:9), FLLPHPGLQV (SEQ ID NO:10), LLNMPPAHLK (SEQ ID NO:11), TLVDLPGMTKV (SEQ ID NO:13), TLIDLPGITRV (SEQ ID NO:14), LSLDSSLSSLL (SEQ ID NO:17), LLLDVAYGAVQA (SEQ ID NO:22), FLASESLLKGAL (SEQ ID NO:23), LVLNLLE (SEQ ID NO:32), TLVDLPGM (SEQ ID NO:40), IDLPGITR (SEQ ID NO:61), WLTVLFIFRI (SEQ ID NO:66), LVYLGHVIYL (SEQ ID NO:67), FVPEVSFEL (SEQ ID NO:70), and FQMEQIVYC (SEQ ID NO:72); and wherein the activated T lymphocytes are cytotoxic to multiple myeloma cancer cells.

In a third embodiment, the present invention comprises a method for creating activated T lymphocytes for administration to a patient diagnosed with multiple myeloma, the method comprising the steps of: (a) preparing antigenic peptide loaded *Drosophila* artificial antigen presenting cells (aAPCs) by loading *Drosophila* aAPCs with at least one antigenic peptide, wherein the antigenic peptide comprises an amino acid sequence selected from the group consisting of: SLVLNLLEL (SEQ ID NO:3), KNPVLLKIL (SEQ ID NO:7), NLLPKLHVV (SEQ ID NO:9), FLLPHPGLQV (SEQ ID NO:10), LLNMPPAHLK (SEQ ID NO:11), TLVDLPGMTKV (SEQ ID NO:13), TLIDLPGITRV (SEQ ID NO:14), LSLDSSLSSLL (SEQ ID NO:17), LLLDVAYGAVQA (SEQ ID NO:22), FLASESLLKGAL (SEQ ID NO:23), LVLNLLE (SEQ ID NO:32), TLVDLPGM (SEQ ID NO:40), IDLPGITR (SEQ ID NO:61), WLTVLFIFRI (SEQ ID NO:66), LVYLGHVIYL (SEQ ID NO:67), FVPEVSFEL (SEQ ID NO:70), and FQMEQIVYC (SEQ ID NO:72); (b) isolating T lymphocytes from the patient; (c) contacting said T lymphocytes with said antigenic peptide loaded *Drosophila* aAPCs; (d) generating activated T lymphocytes, wherein the activated T lymphocytes are cytotoxic to multiple myeloma cancer cells; and, (e) collecting the activated T lymphocytes for administration back to the patient.

In a fourth embodiment, the present invention comprises the method described above, further comprising the step of: (f) administering to said patient an effective amount of the activated T lymphocytes collected in said collecting step.

In a fifth embodiment, the present invention comprises a method for creating activated T lymphocytes for administration to a patient diagnosed with multiple myeloma, the method comprising the steps of: (a) preparing antigenic peptide loaded *Drosophila* artificial antigen presenting cells (aAPCs) by loading *Drosophila* aAPCs with a mixture of two or more antigenic peptides, wherein the antigenic peptides comprise an amino acid sequence selected from the group consisting of: SLVLNLLEL (SEQ ID NO:3), KNPVLLKIL (SEQ ID NO:7), NLLPKLHVV (SEQ ID NO:9), FLLPHPGLQV (SEQ ID NO:10), LLNMPPAHLK (SEQ ID NO:11), TLVDLPGMTKV (SEQ ID NO:13), TLIDLPGITRV (SEQ ID NO:14), LSLDSSLSSLL (SEQ ID NO:17), LLLDVAYGAVQA (SEQ ID NO:22), FLAS- ESLLKGAL (SEQ ID NO:23), LVLNLLE (SEQ ID NO:32), TLVDLPGM (SEQ ID NO:40), IDLPGITR (SEQ ID NO:61), WLTVLFIFRI (SEQ ID NO:66), LVYLGHVIYL (SEQ ID NO:67), FVPEVSFEL (SEQ ID NO:70), and FQMEQIVYC (SEQ ID NO:72); (b) isolating T lymphocytes from the patient; (c) contacting said T lymphocytes with said antigenic peptide loaded *Drosophila* aAPCs; (d) generating activated T lymphocytes, wherein the activated T lymphocytes are cytotoxic to multiple myeloma cancer cells; and, (e) collecting the activated T lymphocytes for administration back to the patient.

In a sixth embodiment, the present invention comprises the method described above, wherein the mixture of two or more antigenic peptides comprises a composition containing SEQ ID NO:3, SEQ ID NO:13, and SEQ ID NO:14.

In a seventh embodiment, the present invention comprises an ex vivo method for creating activated T lymphocytes for administration to a patient diagnosed with multiple myeloma, the method comprising the steps of: (a) preparing antigenic peptide loaded *Drosophila* artificial antigen presenting cells (aAPCs) by loading *Drosophila* aAPCs with at least one antigenic peptide, wherein the antigenic peptide comprises an amino acid sequence selected from the group consisting of: SLVLNLLEL (SEQ ID NO:3), KNPVLLKIL (SEQ ID NO:7), NLLPKLHVV (SEQ ID NO:9), FLLPHPGLQV (SEQ ID NO:10), LLNMPPAHLK (SEQ ID NO:11), TLVDLPGMTKV (SEQ ID NO:13), TLIDLPGITRV (SEQ ID NO:14), LSLDSSLSSLL (SEQ ID NO:17), LLLDVAYGAVQA (SEQ ID NO:22), FLASESLLKGAL (SEQ ID NO:23), LVLNLLE (SEQ ID NO:32), TLVDLPGM (SEQ ID NO:40), IDLPGITR (SEQ ID NO:61), WLTVLFIFRI (SEQ ID NO:66), LVYLGHVIYL (SEQ ID NO:67), FVPEVSFEL (SEQ ID NO:70), and FQMEQIVYC (SEQ ID NO:72); (b) isolating T lymphocytes from the patient; (c) contacting said T lymphocytes with said antigenic peptide loaded *Drosophila* aAPCs; (d) generating activated T lymphocytes, wherein the activated T lymphocytes are cytotoxic to multiple myeloma cancer cells; and, (e) collecting the activated T lymphocytes for administration back to the patient; and, (f) restimulating said activated T lymphocytes, said restimulating procedure comprising: (i) contacting the activated T lymphocytes with at least one cytokine selected from the group consisting of: IL-2, IL-4, IL-7, IL-12, IL-15, IL-17, IL-21, IFN-g, and TNF-α, thereby promoting activated T cell growth, proliferation, and/or differentiation; and, (ii) incubating the activated T cells with irradiated autologous non-CD8+ cells, adherent nonCD8+ cells, or antigenic peptide loaded *Drosophila* aAPCs, thereby generating restimulated activated T lymphocytes.

In an eighth embodiment, the present invention comprises the method described above, wherein said restimulating procedure comprises: (i) contacting the activated T lymphocytes with a combination of IL-2 and at least one other cytokine selected from the group consisting of: IL-7, IL-15 or IL-21 thereby promoting activated T cell growth, proliferation, and/ or differentiation; and, (ii) incubating the activated T cells with irradiated autologous non CD8+ cells, adherent nonCD8+ cells, or antigenic peptide loaded *Drosophila* aAPCs, thereby generating restimulated activated T lymphocytes.

In an ninth embodiment, the present invention comprises the method described above, wherein said restimulating procedure comprises: contacting the activated T lymphocytes with antigenic peptide loaded *Drosophila* aAPCs in the presence of IL-2 at a concentration of from 1 to 100 U/ml; IL-7 from 1 to 100 U/ml, IL-15 from 1 to 100 ng/ml and IL-21 from 1 to 100 ng/ml.

BRIEF DESCRIPTION OF THE DRAWINGS

Embodiments of the present invention will now be described, by way of an example only, with reference to the accompanying drawings wherein.

DETAILED DESCRIPTION OF ILLUSTRATIVE EMBODIMENTS

Figure 1:
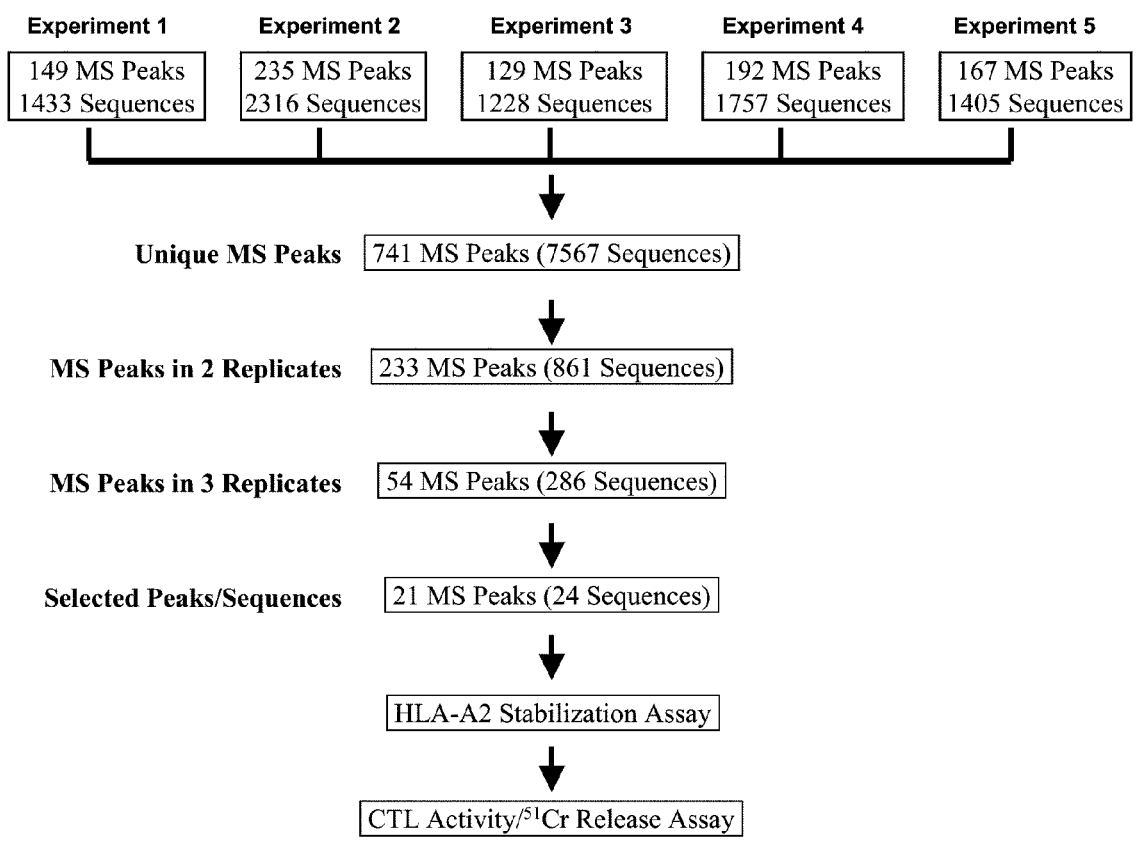
FIG. 1: Shown is a schematic representation of the peptide identification process, including selection of the LC/MS/MS peaks to identify the peptides, testing of the peptides for peptide binding in the HLA-A2 Stabilization Assay, and testing CTL activity in the $^{51}$Cr Release Assay.
Figure 2A:
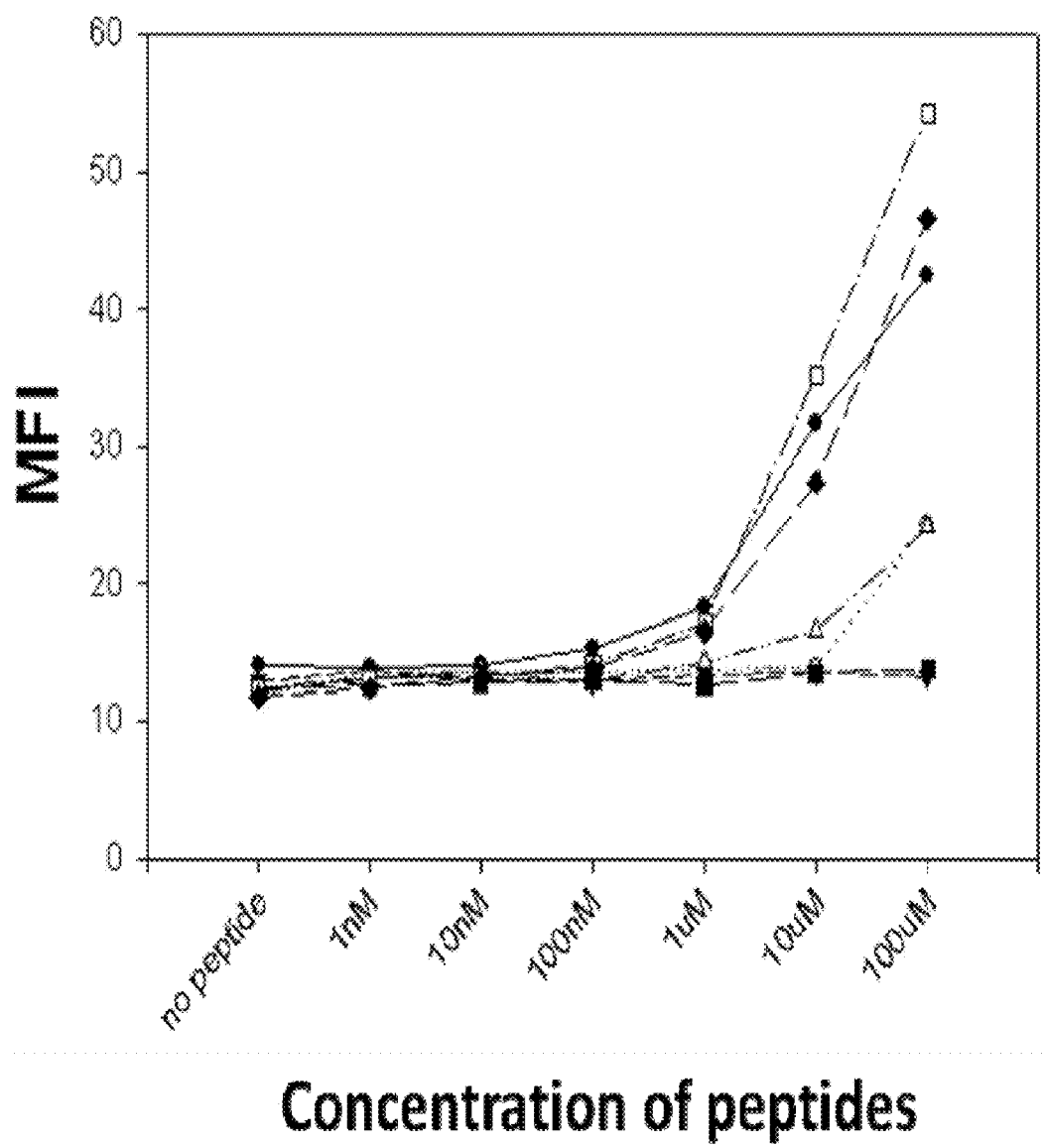
FIG. 2: Shown are graphs of Median Fluorescence Intensities (MFI) vs. peptide concentrations for the 24 selected peptides that were synthesized and assayed for their ability to bind and stabilize HLA-A2 molecules in T2 cells. A peptide of HBC (Hepatitis B Core protein) was used as a positive control. Shown in (A) are results for the HBC control peptide and peptides 1 to 6 (P1 to P6) labeled as follows: HBC (filled circle), P1 (open circle), P2 (filled triangle), P3 (open triangle), P4 (filled square), P5 (open square), and P6 (filled diamond). Shown in (B) are results for the control peptide (HBC) and peptides 7 to 12 (P7 to P12) labeled as follows: HBC (filled circle), P7 (open circle), P8 (filled triangle), P9 (open triangle), P10 (filled square), P11 (open square), and P12 (filled diamond). Shown in (C) are results for the control peptide (HBC) and peptides 13 to 18 (P13 to P18) labeled as follows: HBC (filled circle), P13 (open circle), P14 (filled triangle), P15 (open triangle), P16 (filled square), P17 (open square), and P18 (filled diamond). Shown in (D) are results for the control peptide (HBC) and peptides 19 to 24 (P19 to P24) labeled as follows: HBC (filled circle), P19 (open circle), P20 (filled triangle), P21 (open triangle), P22 (filled square), P23 (open square), and P24 (filled diamond).
Figure 2B:
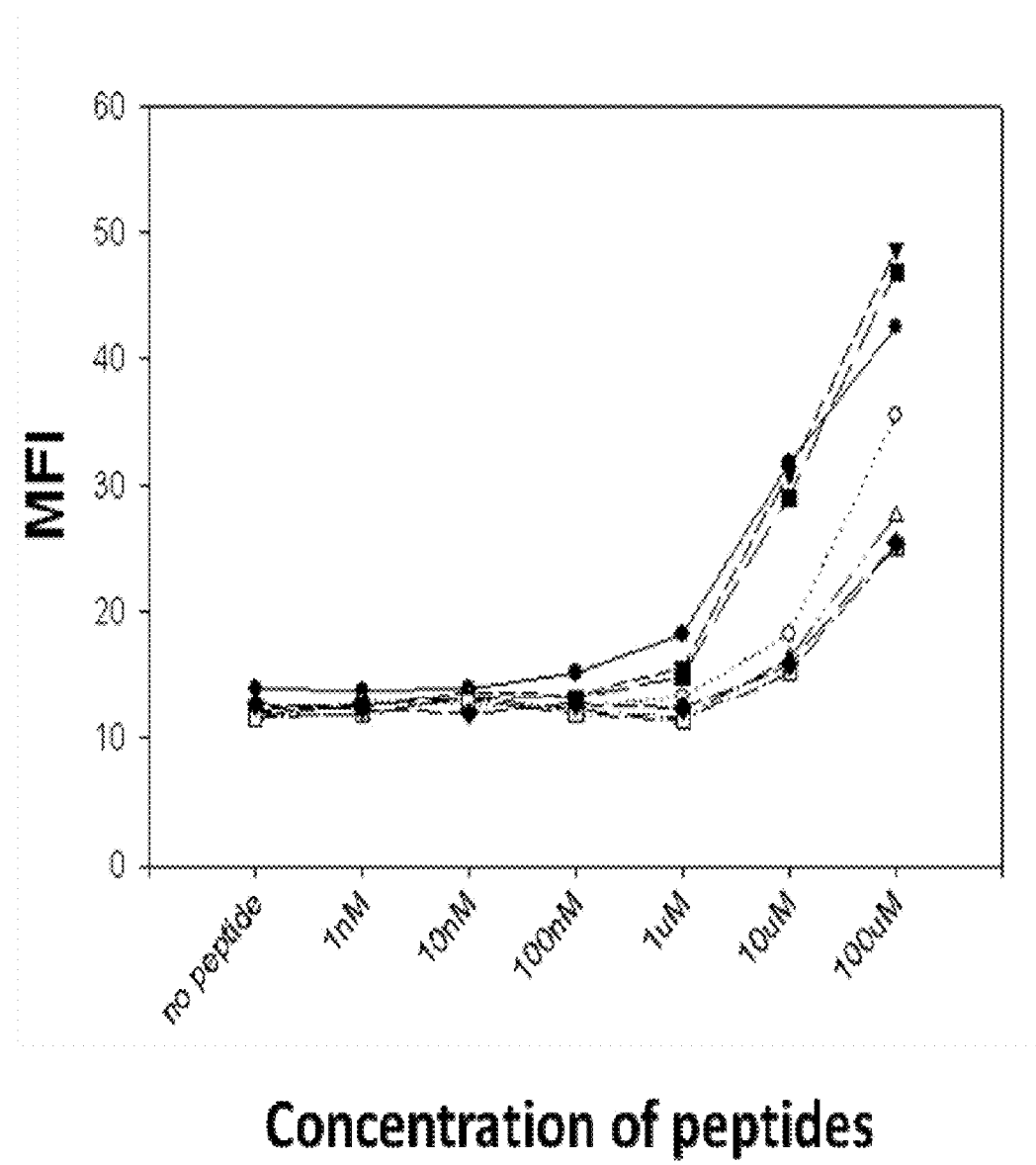
Figure 2C:
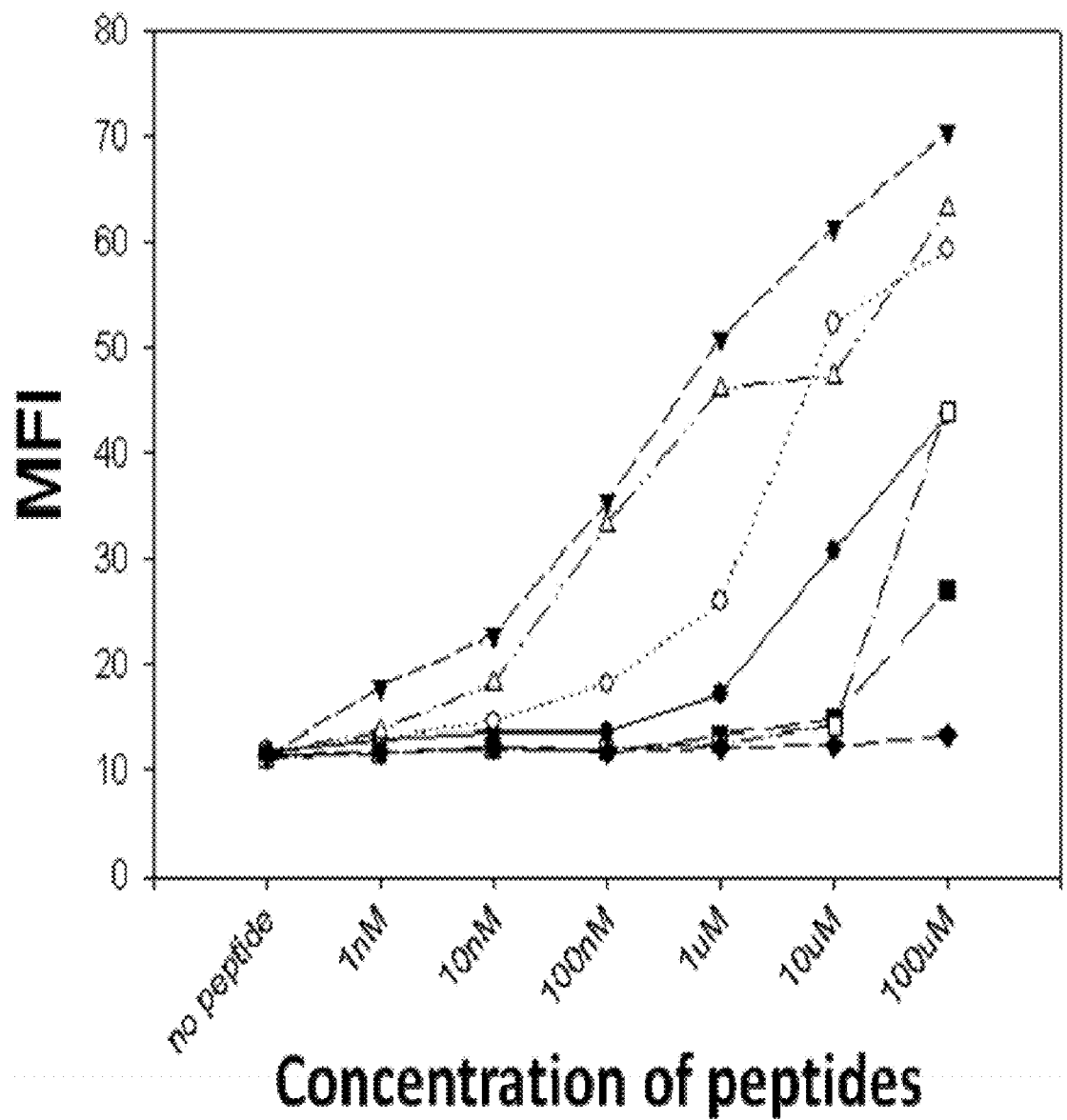
Figure 2D:
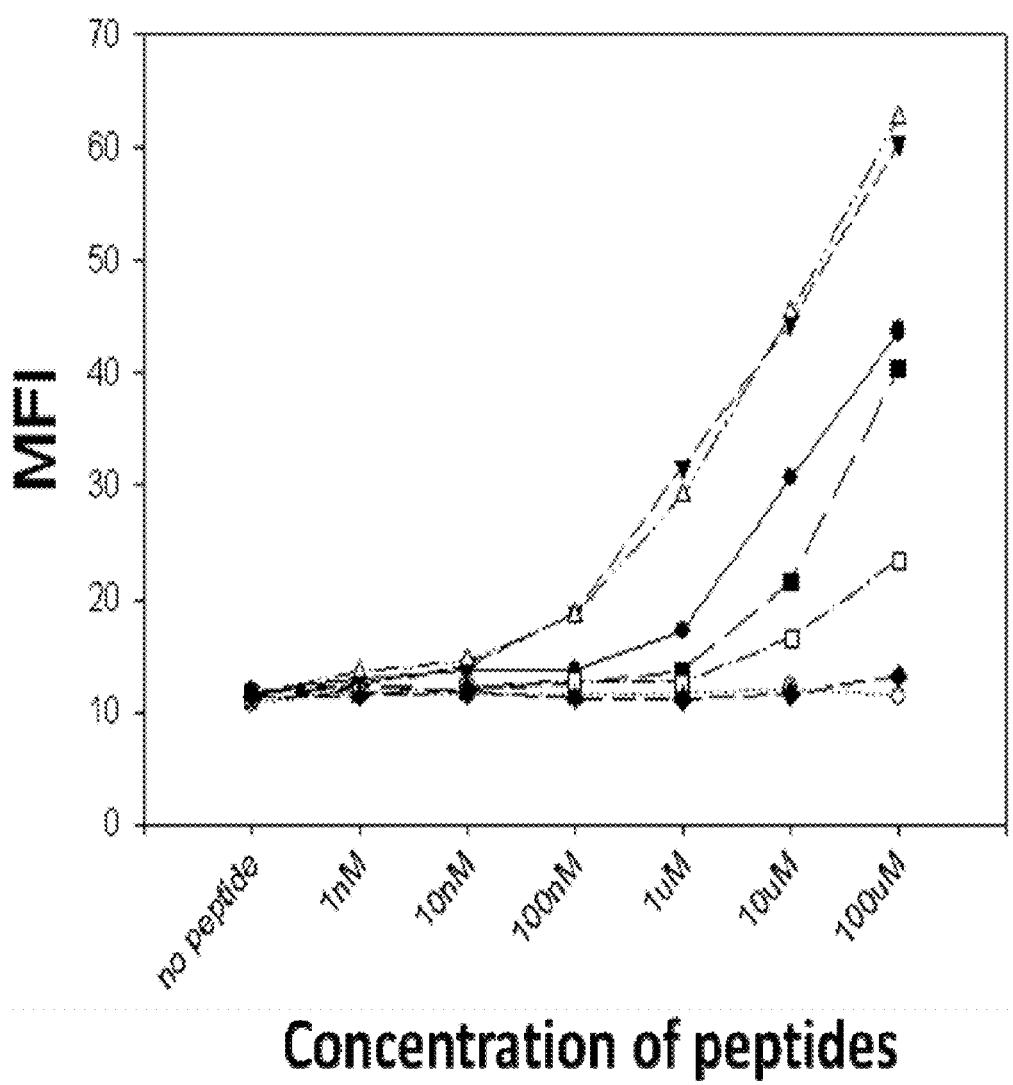
Figure 3A:
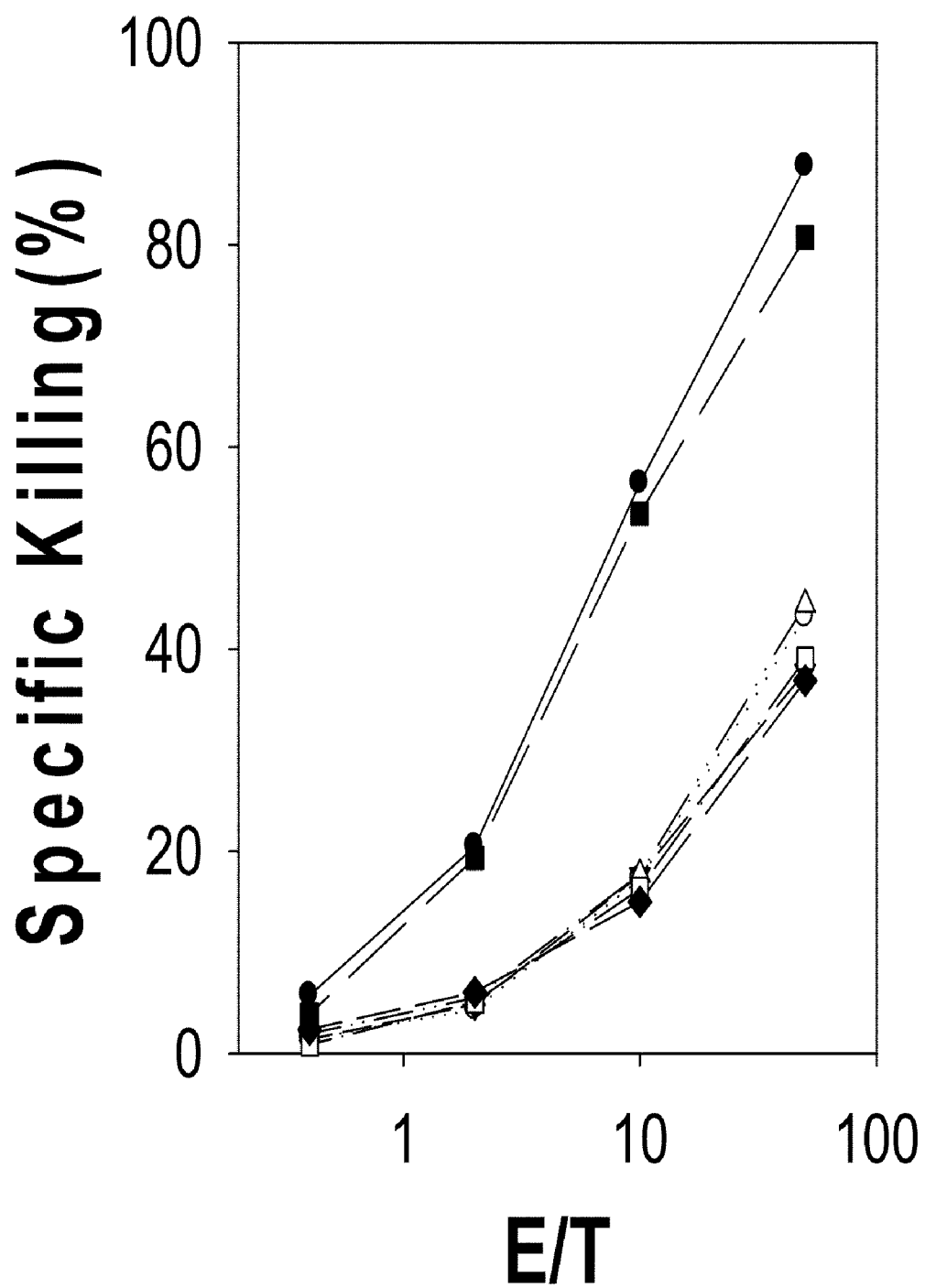
FIG. 3: Shown are graphs of CTL activities measured in the $^{51}$Cr Release Assay. 5 different batches of CTL were generated from a single HLA-A2 positive donor (Donor 1). 24 selected peptides were mixed or used individually to create different combinations of peptide mixtures (PM) or individual peptides (P) for both generating CTL and for loading T2 cells. The activities for the different CTL were measured in the $^{51}$Cr Release Assay with T2 cells loaded with the individual peptides or the same peptide mixture that was used to generate each CTL. Data are shown as Specific Killing (%) vs. Effector (E) Target (T) ratio (E/T). Shown in (A) are results for CTL generated with peptide mixture 1 (PM1), the mixture containing peptides P1, P7, P9, and P12. CTL activity was measured for T2 cells loaded with no peptide, HBC control peptide, individual peptides P1, P7, P9, or 12, or a peptide mixture PM1 containing peptides P1, P7, P9, and P12. Graphs of Specific Killing (%) for T2 cells loaded with each peptide or peptide mixture are labeled as follows: P1 (filled circle), P7 (open circle), P9 (closed triangle), P12 (open triangle), PM1 (closed square), HBC (open square), and no peptide (filled diamond). Shown in (B) are results for CTL generated with peptide mixture 2 (PM2), the mixture containing peptides P13, P17, and P21. CTL activity was measured for T2 cells loaded with no peptide, HBC control peptide, individual peptides P13, P17, or 21, or a peptide mixture PM2 containing peptides P13, P17, and P21. Graphs of Specific Killing (%) for T2 cells loaded with each peptide or peptide mixture are labeled as follows: P13 (filled circle), P17 (open circle), P21 (closed triangle), PM2 (open triangle), HBC (closed square), no peptide (open square). Shown in (C) are results for CTL generated with peptide mixture 3 (PM3), the mixture containing peptides P5, P6, P8, and P10. CTL activity was measured for T2 cells loaded with no peptide, HBC control peptide, individual peptides P5, P6, P8, or 10, or a peptide mixture PM3 containing peptides P5, P6, P8, and P10. Graphs of Specific Killing (%) for T2 cells loaded with each peptide or peptide mixture are labeled as follows: P5 (filled circle), P6 (open circle), P8 (closed triangle), P10 (open triangle), PM3 (closed square), HBC (open square), and no peptide (filled diamond). Shown in (D) are results for CTL generated with peptide mixture 4 (PM4), the mixture containing peptides P14, P15, and P20. CTL activity was measured for T2 cells loaded with no peptide, HBC control peptide, individual peptides P14, P15, or 20, or a peptide mixture PM4 containing peptides P14, P15, and P20. Graphs of Specific Killing (%) for T2 cells loaded with each peptide or peptide mixture are labeled as follows: P14 (filled circle), P15 (open circle), P20 (closed triangle), PM4 (open triangle), HBC (closed square), no peptide (open square). Shown in (E) are results for CTL generated with peptide 14. CTL activity was measured for T2 cells loaded with no peptide, HBC control peptide, or the individual P14 peptide. Graphs of Specific Killing (%) for T2 cells loaded with each peptide are labeled as follows: P14 (filled circle), HBC (open circle), and no peptide (closed triangle).
Figure 3B:
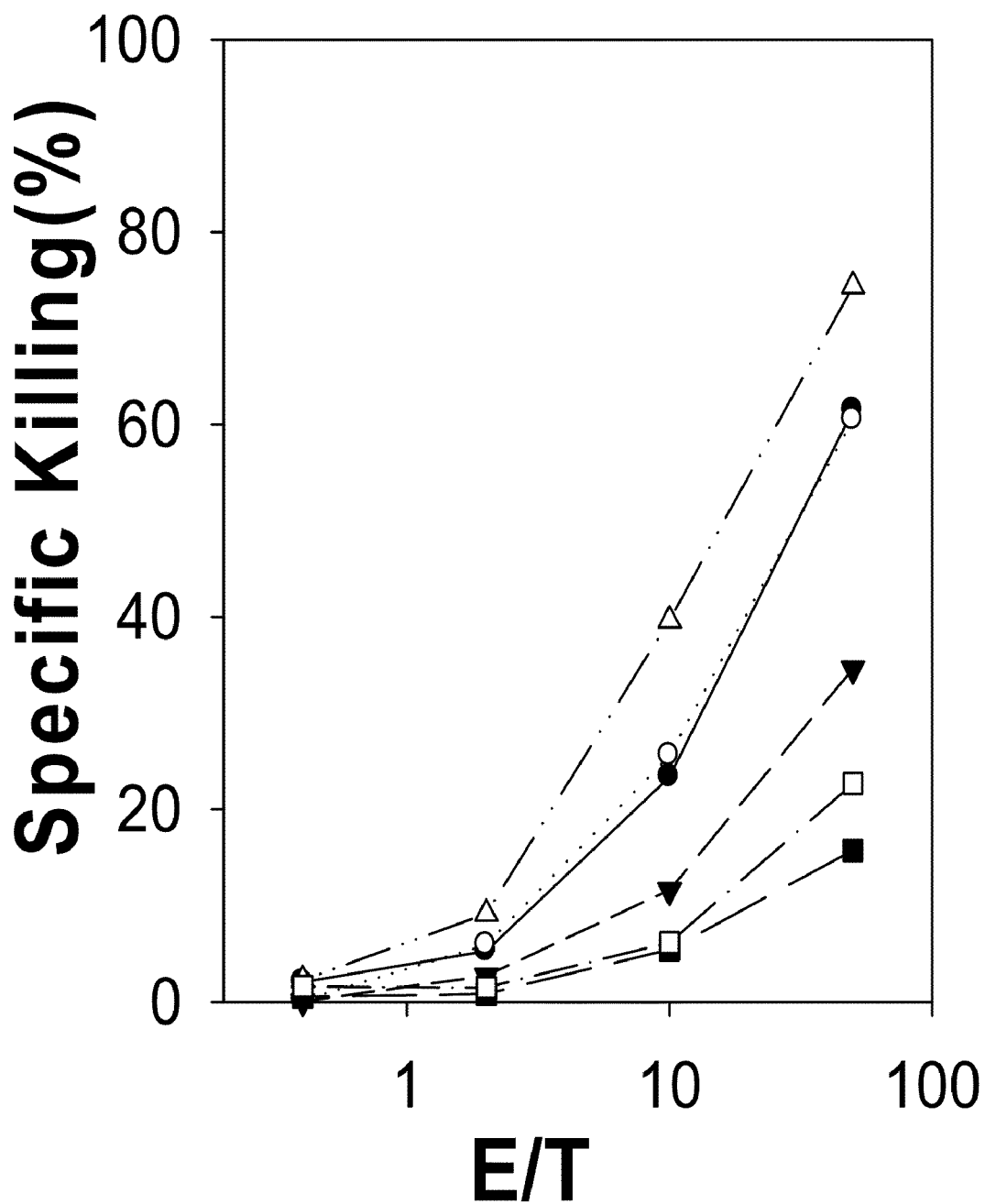
Figure 3C:
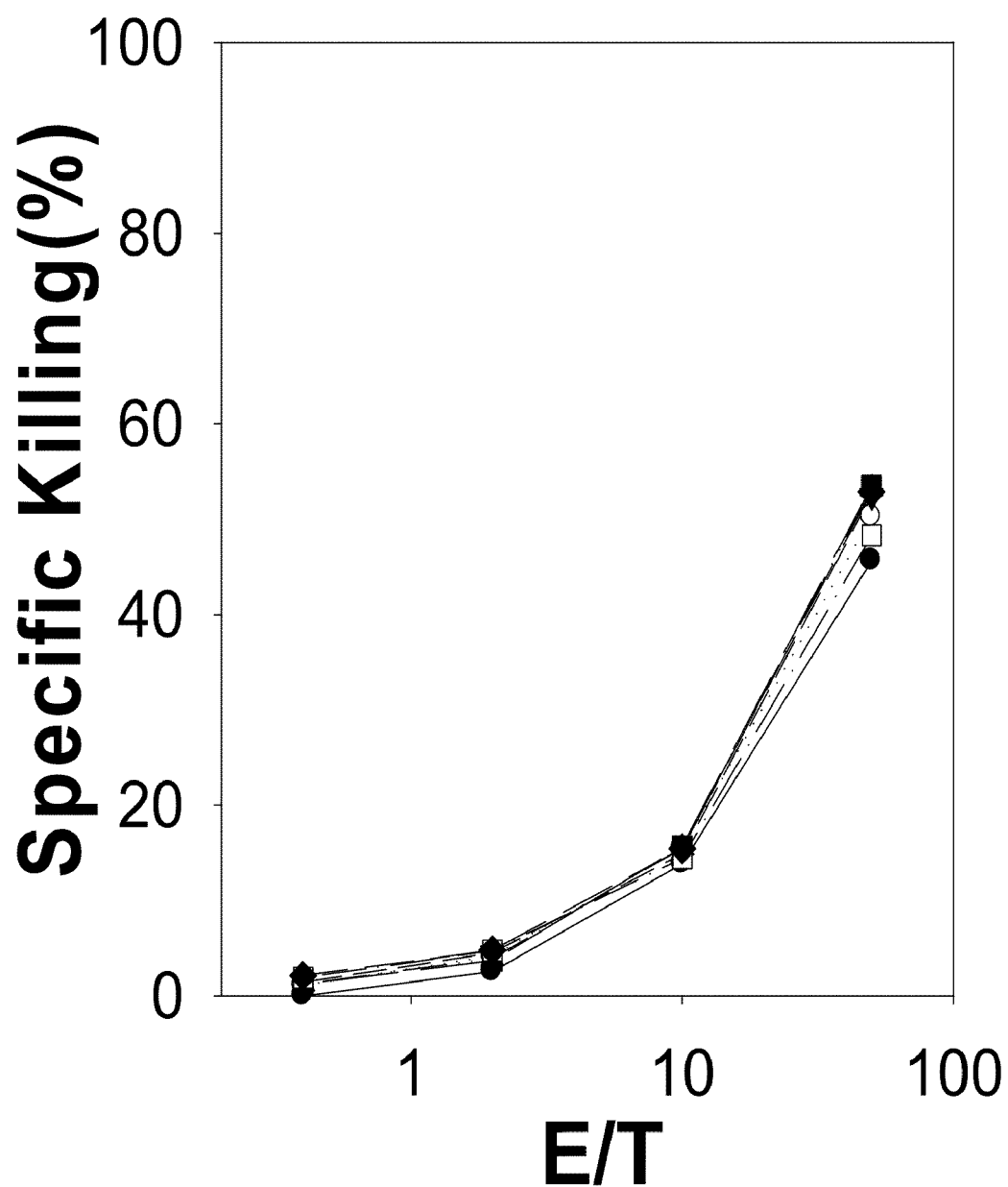
Figure 3D:
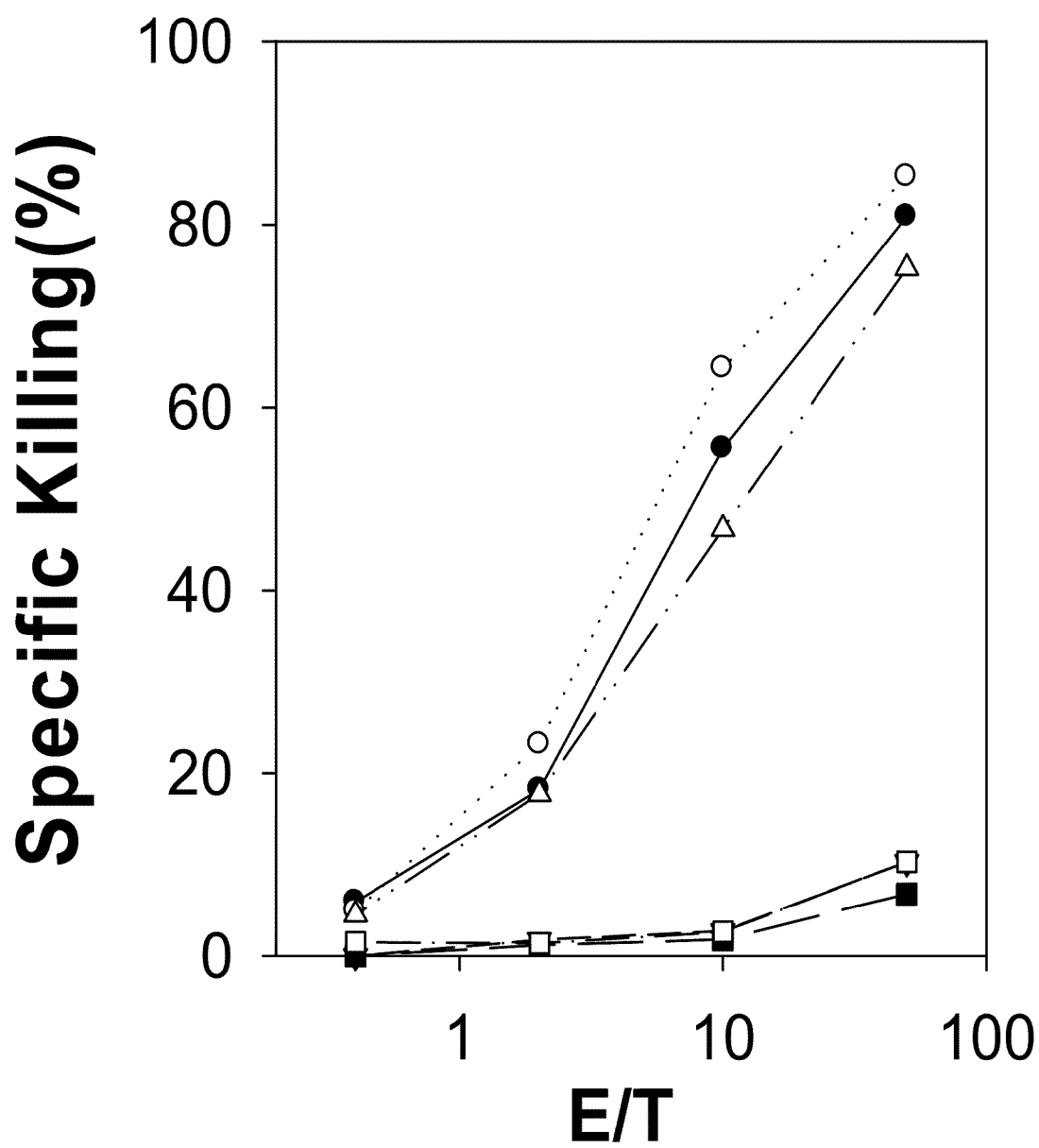
Figure 3E:
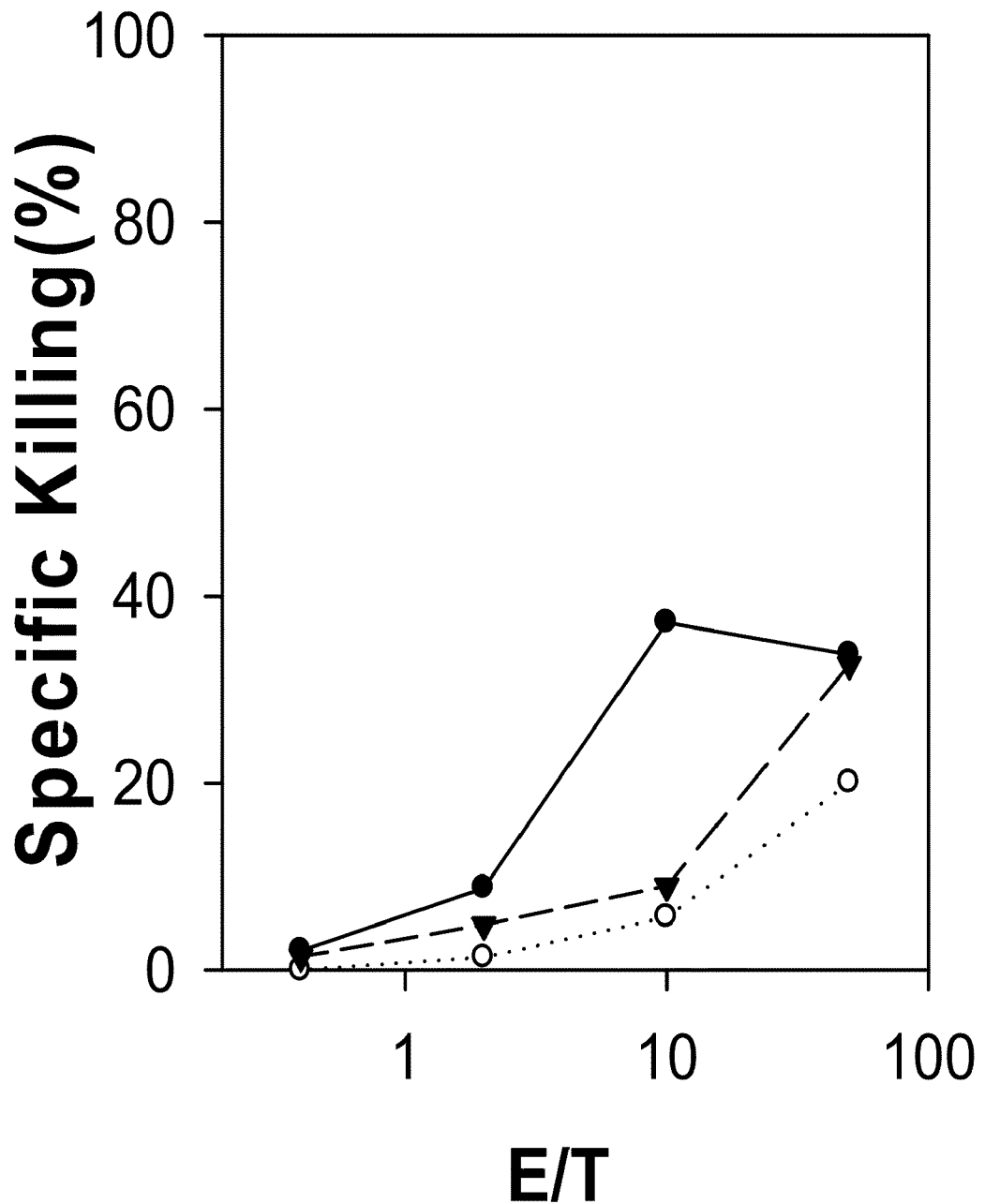
Figure 4A:
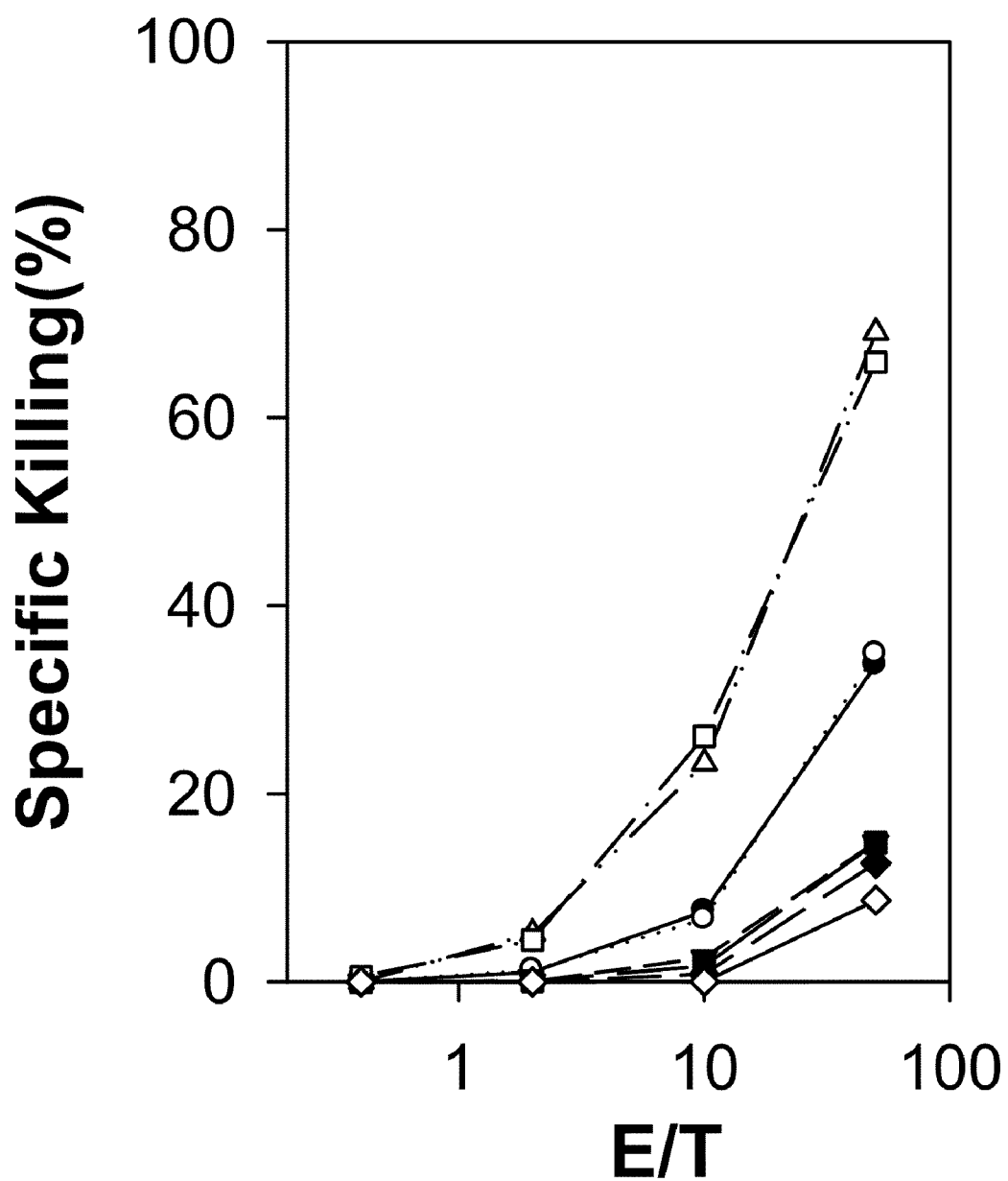
FIG. 4: Shown are graphs of CTL activities measured in the $^{51}$Cr Release Assay. 6 different batches of CTL were generated from a single HLA-A2 positive donor (Donor 2). 24 selected peptides were mixed or used individually to create different combinations of peptide mixtures (PM) or individual peptides (P) for both generating CTL and for loading T2 cells. The activities for the different CTL were measured in the $^{51}$Cr Release Assay with T2 cells loaded with the individual peptides or the same peptide mixture that was used to generate each CTL. Data are shown as Specific Killing (%) vs. Effector (E) Target (T) ratio (E/T). Shown in (A) are results for CTL generated with peptide mixture 1 (PM1), the mixture containing peptides P5, P6, P8, P10, and P13. CTL activity was measured for T2 cells loaded with no peptide, HBC control peptide, individual peptides P5, P6, P8, P10, or P13, or a peptide mixture PM1 containing peptides P5, P6, P8, P10, and P13. Graphs of Specific Killing (%) for T2 cells loaded with each peptide or peptide mixture are labeled as follows: P5 (filled circle), P6 (open circle), P8 (closed triangle), P10 (open triangle), P13 (closed square), PM1 (open square), HBC (filled diamond), and no peptide (open diamond). Shown in (B) are results for CTL generated with peptide mixture 2 (PM2), the mixture containing peptides P14, P15, P17, P20 and P21. CTL activity was measured for T2 cells loaded with no peptide, HBC control peptide, individual peptides P14, P15, P17, P20 or P21, or a peptide mixture PM2 containing peptides P14, P15, P17, P20 and P21. Graphs of Specific Killing (%) for T2 cells loaded with each peptide or peptide mixture are labeled as follows: P14 (filled circle), P15 (open circle), P17 (closed triangle), P20 (open triangle), P21 (closed square), PM2 (open square), HBC (closed diamond), no peptide (open diamond). Shown in (C) are results for CTL generated with peptide mixture 3 (PM3), the mixture containing peptides P1, P3, P7, P9, and P11. CTL activity was measured for T2 cells loaded with no peptide, HBC control peptide, individual peptides P1, P3, P7, P9, or P11, or a peptide mixture PM3 containing peptides P1, P3, P7, P9, and P11. Graphs of Specific Killing (%) for T2 cells loaded with each peptide or peptide mixture are labeled as follows: P1 (filled circle), P3 (open circle), P7 (closed triangle), P9 (open triangle), P11 (closed square), PM3 (open square), HBC (filled diamond), and no peptide (open diamond). Shown in (D) are results for CTL generated with peptide mixture 4 (PM4), the mixture containing peptides P12, P16, P22, and P23. CTL activity was measured for T2 cells loaded with no peptide, HBC control peptide, individual peptides P12, P16, P22, or P23, or a peptide mixture PM4 containing peptides P12, P16, P22, and P23. Graphs of Specific Killing (%) for T2 cells loaded with each peptide or peptide mixture are labeled as follows: P12 (filled circle), P16 (open circle), P22 (closed triangle), P23 (open triangle), PM4 (closed square), HBC (open square), and no peptide (closed triangle). Shown in (E) are results for CTL generated with peptide 5. CTL activity was measured for T2 cells loaded with no peptide, HBC control peptide, or the individual P5 peptide. Graphs of Specific Killing (%) for T2 cells loaded with each peptide are labeled as follows: P5 (filled circle), HBC (open circle), and no peptide (closed triangle). Shown in (F) are results for CTL generated with peptide 14. CTL activity was measured for T2 cells loaded with no peptide, HBC control peptide, or the individual P14 peptide. Graphs of Specific Killing (%) for T2 cells loaded with each peptide are labeled as follows: P14 (filled circle), HBC (open circle), and no peptide (closed triangle).
Figure 4B:
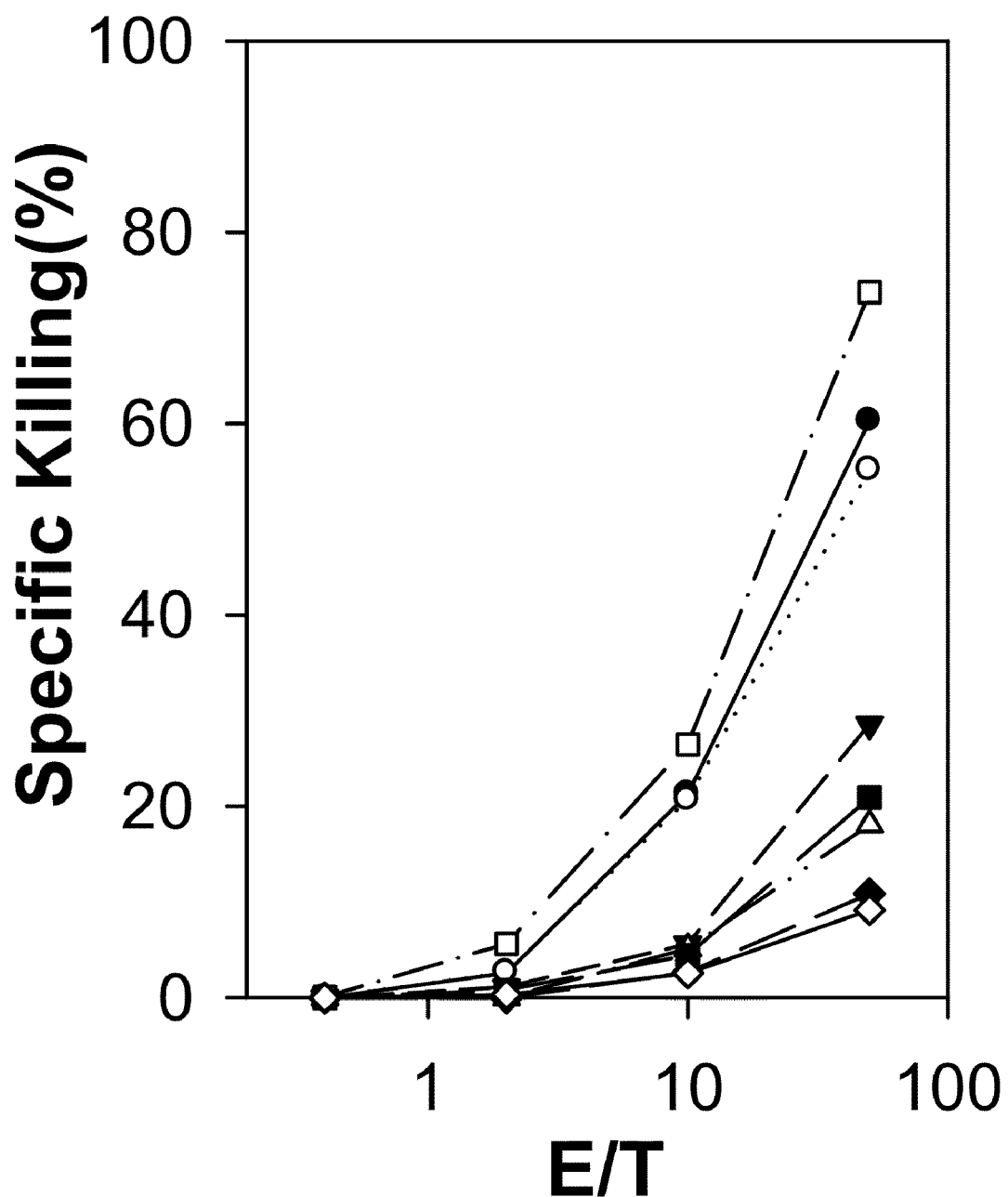
Figure 4C:
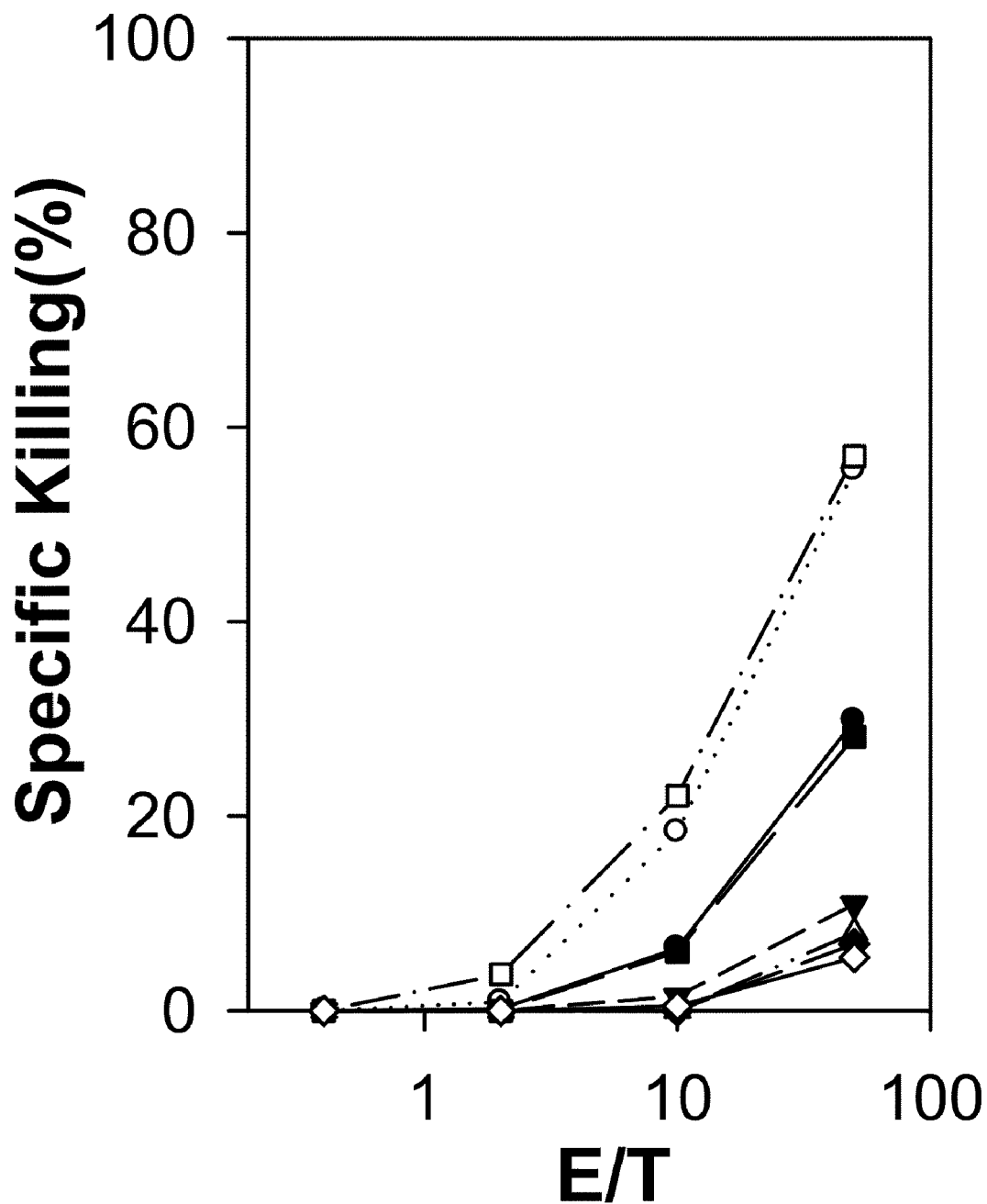
Figure 4D:
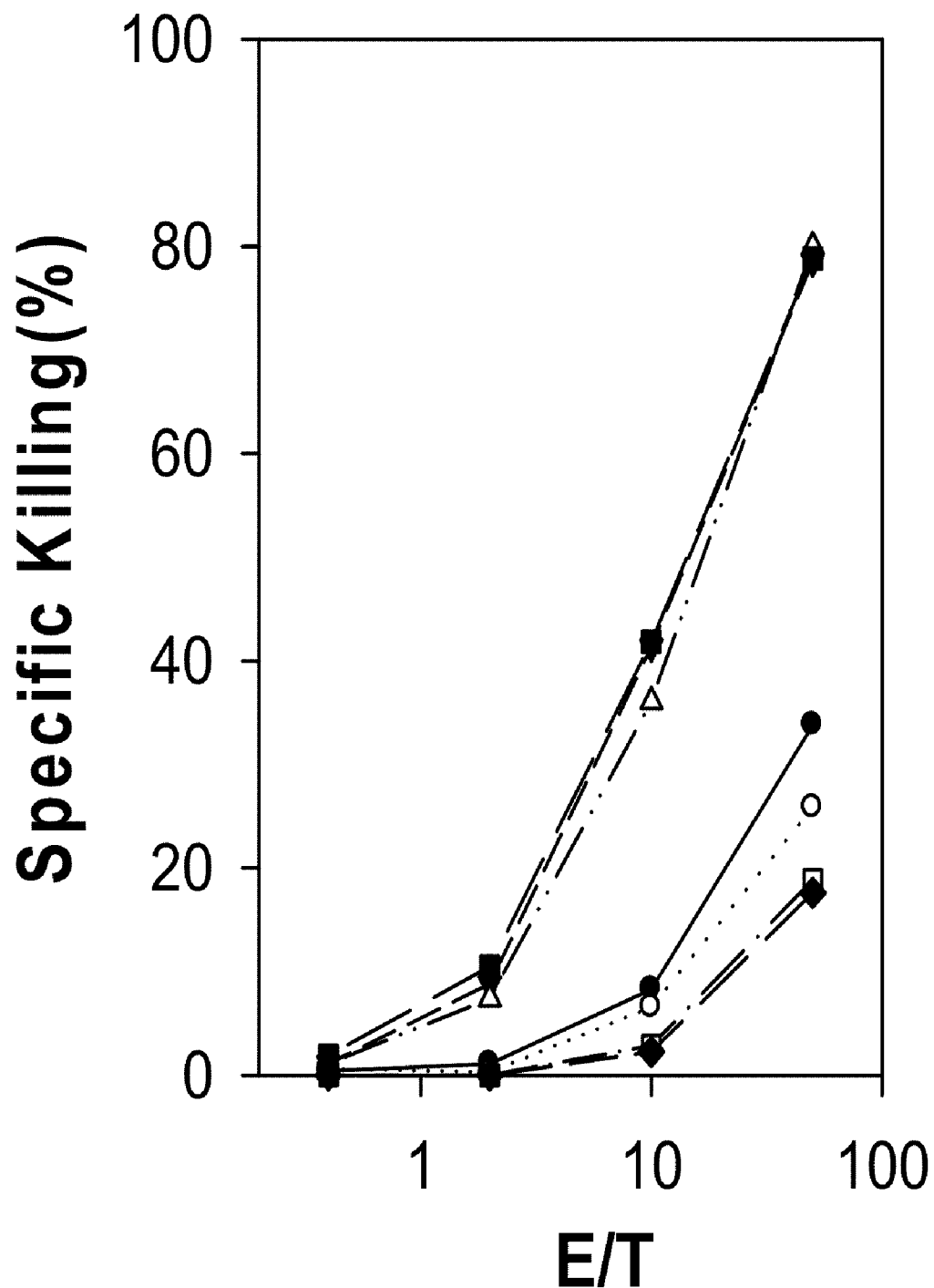
Figure 4E:
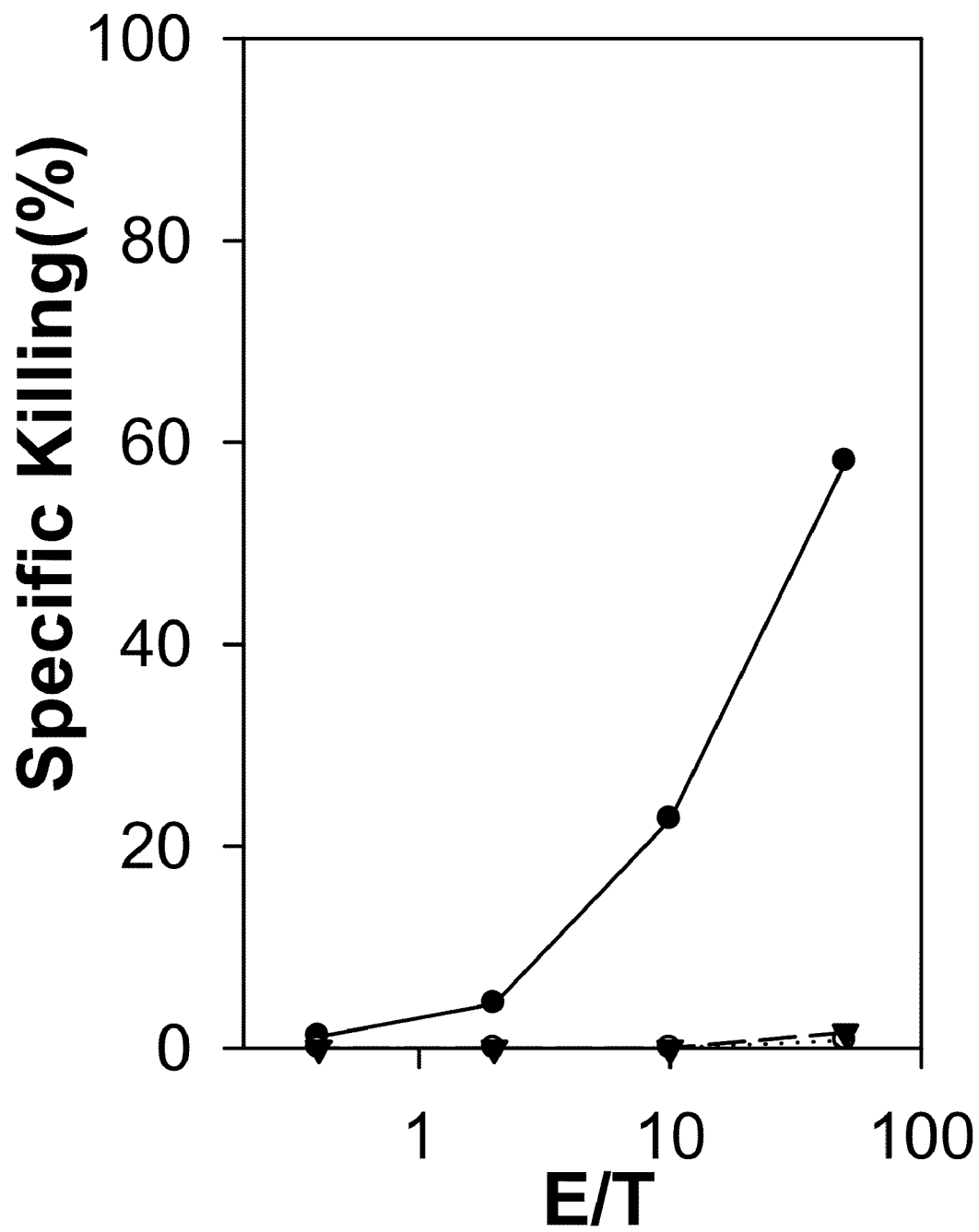
Figure 4F:
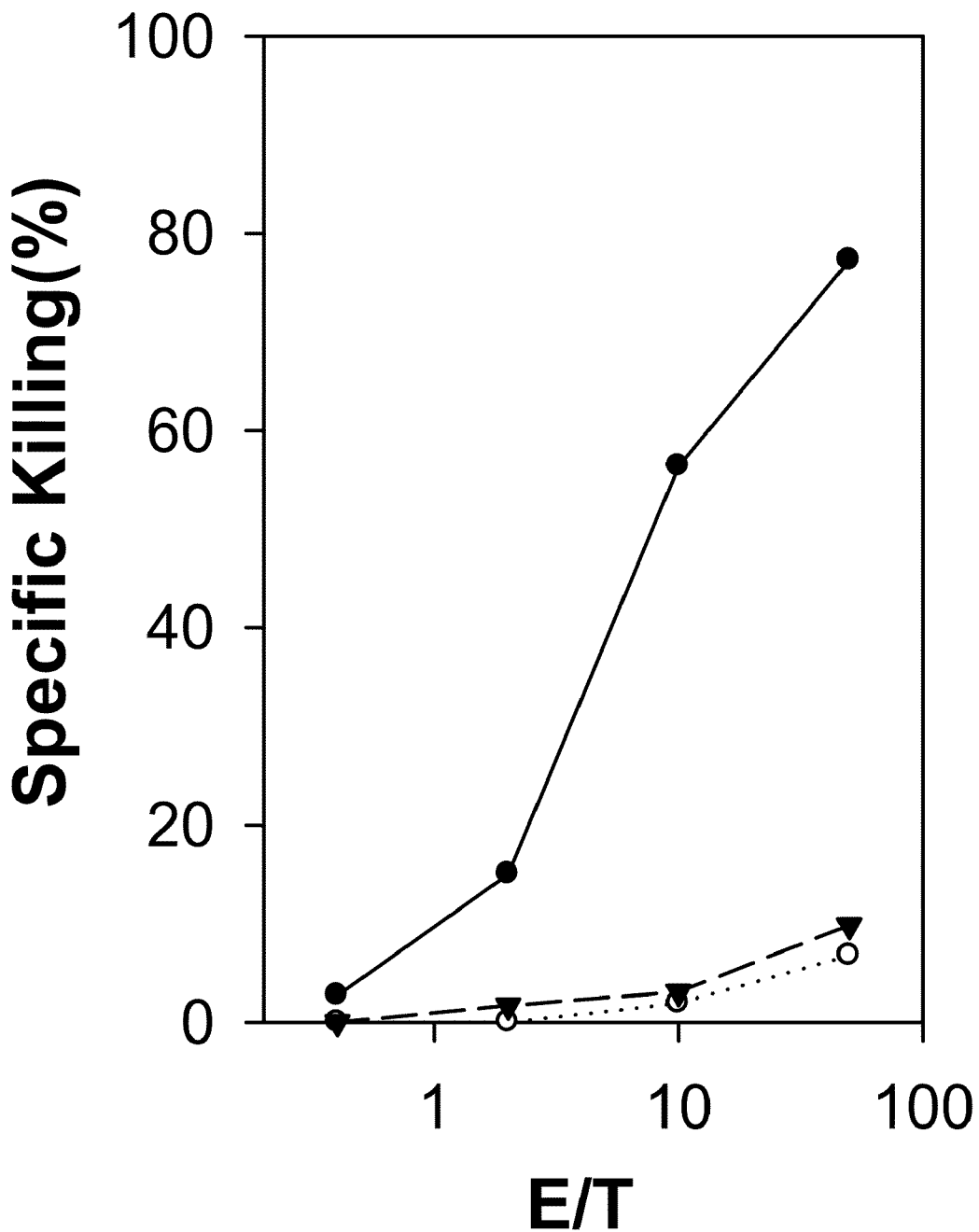

To illustrate the invention, various exemplary embodiments are described below.

In the present invention HLA-A2 associated peptides were purified from a multiple myeloma (MM) cell line (U266) by immunoaffinity-purification of HLA-A2 molecules. The amino acid sequences of the peptides were determined after systematic identification of peaks by liquid chromatography tandem mass spectrometry (LC/MS/MS) and de novo sequencing using LC/MS/MS. Antigenic peptides of the present invention activated CD8+ T cells and activated T cells killed both peptide loaded T2 target cells and multiple myeloma cell lines.

Peptides

The present invention relates to a composition comprising at least one antigenic peptide, wherein the antigenic peptide comprises an amino acid sequence selected from the group consisting of: SLVLNLLEL (SEQ ID NO:3), KNPVLLKIL (SEQ ID NO:7), NLLPKLHVV (SEQ ID NO:9), FLLPHPGLQV (SEQ ID NO:10), LLNMPPAHLK (SEQ ID NO:11), TLVDLPGMTKV (SEQ ID NO:13), TLIDLPGITRV (SEQ ID NO:14), LSLDSSLSSLL (SEQ ID NO:17), LLLDVAYGAVQA (SEQ ID NO:22), FLAS- ESLLKGAL (SEQ ID NO:23), LVLNLLE (SEQ ID NO:32), TLVDLPGM (SEQ ID NO:40), IDLPGITR (SEQ ID NO:61), WLTVLFIFRI (SEQ ID NO:66), LVYLGHVIYL (SEQ ID NO:67), FVPEVSFEL (SEQ ID NO:70), FQMEQIVYC (SEQ ID NO:72); wherein the antigenic peptide is capable of activating T lymphocytes and the activated T lymphocytes are cytotoxic to multiple myeloma cancer cells.

The above referenced composition can comprise a mixture of two or more antigenic peptides.

The present invention also relates to a composition comprising a mixture of two or more antigenic peptides, wherein at least one of the antigenic peptides of the mixture is selected from the group consisting of: SLVLNLLEL (SEQ ID NO:3), KNPVLLKIL (SEQ ID NO:7), NLLPKLHVV (SEQ ID NO:9), FLLPHPGLQV (SEQ ID NO:10), LLNMPPAHLK (SEQ ID NO:11), TLVDLPGMTKV (SEQ ID NO:13), TLIDLPGITRV (SEQ ID NO:14), LSLDSSLSSLL (SEQ ID NO:17), LLLDVAYGAVQA (SEQ ID NO:22), FLASESLLKGAL (SEQ ID NO:23), LVLNLLE (SEQ ID NO:32), TLVDLPGM (SEQ ID NO:40), IDLPGITR (SEQ ID NO:61), WLTVLFIFRI (SEQ ID NO:66), LVYLGHVIYL (SEQ ID NO:67), FVPEVSFEL (SEQ ID NO:70), FQMEQIVYC (SEQ ID NO:72) and at least one other antigenic peptide of the mixture is selected from other antigenic peptides known to be associated with cancer or by its ability to induce a CTL response against a cancer cell. For exemplary other antigenic peptides, see, e.g., U.S. Pat. No. 7,402,314 and U.S. Patent Application Publication No. 2009/0017000.

Peptides that are naturally processed and bound to a class I MHC molecule, and which are recognized by a tumor-specific CTL, are not necessarily the optimal peptides for stimulating a CTL response (see, e.g., Parkhurst, M. R. et al., *J. Immunol.*, 157:2539-2548, 1996; Rosenberg, S. A. et al., *Nat. Med.*, 4:321-327, 1998). Thus, there can be utility in modifying a peptide, such that it more readily induces a CTL response. Generally, peptides may be modified at two types of positions. The peptides may be modified at amino acid residues that are predicted to interact with the class I MHC molecule, in which case the goal is to create a peptide that has a higher affinity for the class I MHC molecule than does the original peptide. The peptides can also be modified at amino acid residues that are predicted to interact with the T cell receptor on the CTL, in which case the goal is to create a peptide that has a higher affinity for the T cell receptor than does the original peptide. Both of these types of modifications can result in a variant peptide that is related to an original peptide, but which is better able to induce a CTL response than is the original peptide. As used herein, the term "original peptide" means a peptide with the amino acid sequence selected from the group consisting of: SLVLNLLEL (SEQ ID NO:3), KNPVLLKIL (SEQ ID NO:7), NLLPKLHVV (SEQ ID NO:9), FLLPHPGLQV (SEQ ID NO:10), LLNMPPAHLK (SEQ ID NO:11), TLVDLPGMTKV (SEQ ID NO:13), TLIDLPGITRV (SEQ ID NO:14), LSLDSSLSSLL (SEQ ID NO:17), LLLDVAYGAVQA (SEQ ID NO:22), FLASESLLKGAL (SEQ ID NO:23), LVLNLLE (SEQ ID NO:32), TLVDLPGM (SEQ ID NO:40), IDLPGITR (SEQ ID NO:61), WLTVLFIFRI (SEQ ID NO:66), LVYLGHVIYL (SEQ ID NO:67), FVPEVSFEL (SEQ ID NO:70), FQMEQIVYC (SEQ ID NO:72).

In studies of sequence variations in families of naturally occurring homologous proteins or peptides, certain amino acid substitutions are more often tolerated than others. Proteins or peptides with these substitutions retain certain characteristics of the original proteins or original peptides. Such changes are referred to as "conservative substitutions". The antigenic peptides disclosed herein can also be modified by a "conservative substitution" of one or more residues at different, possibly selective, sites within the peptide chain. The conservative substitution may include the replacement of an amino acid in the original peptide with another amino acid that is similar compared to the amino acid in the original peptide, with regard to size or chemical nature, such as charge, polarity, or hydrophobicity. For example, one hydrophobic amino acid of the original peptide may be replaced by another hydrophobic amino acid. An even more conservative substitution would be replacement of amino acids of the same or similar size and chemical nature, such as where leucine is replaced by isoleucine.

Conservative substitutions are herein defined as exchanges within one of the following five groups: Group 1 comprising small aliphatic, nonpolar or slightly polar residues (Ala, Ser, Thr, Pro, Gly); Group 2 comprising polar, negatively charged residues and their amides (Asp, Asn, Glu, Gln); Group 3 comprising polar, positively charged residues (His, Arg, Lys); Group 4 comprising large, aliphatic, nonpolar residues (Met, Leu, Ile, Val, Cys); and Group 5 comprising large, aromatic residues (Phe, Tyr, Trp). Other conservative substitutions might involve the replacement of one amino acid by another that has similar characteristics but is somewhat different in size, such as replacement of an alanine by an isoleucine residue.

Of course, such substitutions may also involve structures other than the common L-amino acids. Thus, D-amino acids might be substituted for the L-amino acids commonly found in the antigenic peptides of the present invention and yet still be encompassed by the disclosure herein. In addition, amino acids possessing non-standard R groups (i.e., R groups other than those found in the common 20 amino acids of natural proteins) may also be used for substitution purposes to produce antigenic peptides according to the present invention.

If substitutions at more than one position are found to result in an antigenic peptide with substantially equivalent or greater activity as the original peptide, then combinations of those substitutions will be tested to determine if the combined substitutions result in additive or syngeneic effects on the antigenicity of the peptide. At most, no more than 4 positions within the peptide would simultaneously be substituted.

Based on cytotoxicity assays, a modified or substituted peptide is considered substantially identical to the original peptide if it has 10-fold more or less of the antigenic activity of the original peptide as defined by the ability of the substituted peptide to stimulate a CTL response. Thus, for example, when comparing the lytic activity in the linear portion of the effector:target curves with equimolar concentrations of the original and substituted peptides, the observed percent specific killing of the target cells incubated with the substituted peptide should be equal to that of the original peptide at an effector:target ratio that is no more than 10-fold above or 10-fold below the original peptide effector:target ratio at which the comparison is being made.

Antigenic peptides of the present invention can be prepared synthetically or they can be isolated from natural sources such as tumor cells expressing the original protein product. Regarding antigenic peptides prepared synthetically, the antigenic peptides contemplated herein can be synthesized in solution or on a solid support in accordance with conventional techniques. Various automated peptide synthesizers are commercially available and can be used in accordance with known protocols. See, for example, (Grant, G. A., *Synthetic Peptides: A User's Guide,* 1992, W.H. Freeman and Company, New York; Coligan, J. E. et al, *Current Protocols in Protein Science,* 1999, John Wiley & Sons, Inc., New York).

Fragments of antigenic peptides of the invention can also be synthesized as intermediates in the synthesis of a larger peptide.

Artificial Antigen Presenting Cells (aAPCs)

Antigenic peptides of the present invention are useful for generating artificial antigen presenting cells (aAPCs) loaded with one or more of the antigenic peptides that are capable of activating naïve T cells to become activated T cells (e.g., either activated cluster of differentiation (CD) CD4+ T cells or activated CD8+ T cells, which are activated helper T cells or CTL, respectively) specific for a selected peptide. The aAPCs are useful in preparing therapeutic compositions and cell therapy products comprising activated T cells that have been generated by contacting the peptide-loaded aAPCs. For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009).

The aAPCs that are to be used to generate activated T lymphocytes and stimulate a CTL response are typically incubated with a peptide of an optimal length that allows for direct binding of the peptide to the MHC molecule without additional processing. MHC Class I molecules generally bind peptides that are between 8 to 12 amino acids in length. The most common size is a nonopaptide. Larger peptides, for example those larger than 15 amino acids, have been shown to be less effective in binding to class I MHC molecules. In addition, the specific T cell lineage that is activated by the aAPCs depends on the nature of MHC molecules that are expressed on the surface of the aAPCs. Accordingly, aAPCs expressing only MHC Class I molecules may present selected one or more antigenic peptides to and activate CD8+ T cells, and aAPCs expressing MHC Class II molecules may present selected one or more antigenic peptides to and activate CD4+ T cells. Similarly, aAPCs expressing both MHC Class I and MHC Class II molecules may present selected one or more antigenic peptides to and activate both CD8+ T cells and CD4+ T cells. Selected antigenic peptides may be presented to the cells and loaded onto aAPCs via a variety of means and techniques now known or that become available in the art. Preferably, peptides are added to the aAPC system culture medium.

The aAPCs that are employed in preparing therapeutic compositions and cell therapy products comprising activated T cells of the present invention comprise modified cells from a non-human species that are capable of expressing exogenous molecules on their surface. The aAPCs are made to express exogenous MHC molecules selected from MHC Class I molecules and MHC Class II molecules. An exemplary MHC Class I molecule is HLA-A2.1.

In addition to exogenous MHC molecules, the aAPC systems of the present invention may also comprise at least one exogenous assisting molecule. Any suitable number and combination of assisting molecules may be employed. The assisting molecule facilitates the activation of naïve T-cells when such naïve T cells are presented with an antigenic peptide or other immunogen bound to an MHC Class I or Class II molecule. The assisting molecule may be selected from assisting molecules such as co-stimulatory molecules and adhesion molecules. Exemplary co-stimulatory molecules include CD70 and B7.1 (B7.1 was previously known as B7 and also known as CD80), which among other things, bind to CD28 and/or CTLA-4 molecules on the surface of T cells, thereby affecting, for example, T-cell expansion, Th1 differentiation, short-term T-cell survival, and cytokine secretion such as interleukin (IL)-2 (see Kim et al., 2004, *Nature*, Vol. 22(4), pp. 403-410). Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), that promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001.

Cells selected to become aAPCs, preferably have deficiencies in intracellular antigen-processing, intracellular peptide trafficking, and/or intracellular MHC Class I or Class II molecule-peptide loading, or are poikilothermic (i.e., less sensitive to temperature challenge than mammalian cell lines), or possess both deficiencies and poikilothermic properties. Preferably, cells selected to become aAPCs also lack the ability to express at least one endogenous counterpart (e.g., endogenous MHC Class I or Class II molecule and/or endogenous assisting molecules as described above) to the exogenous MHC Class I or Class II molecule and assisting molecule components that are introduced into the cells. Furthermore, aAPCs preferably retain the deficiencies and poikilothermic properties that were possessed by the cells prior to their modification to generate the aAPCs. Exemplary aAPCs either constitute or are derived from a transporter associated with antigen processing (TAP)-deficient cell line, such as an insect cell line. An exemplary poikilothermic insect cells line is a *Drosophila* cell line, such as a Schneider 2 cell line (see, e.g. Schneider, *J. Embryol. Exp. Morph.* 1972 Vol 27, pp. 353-365). Illustrative methods for the preparation, growth, and culture of Schneider 2 cells, are provided in U.S. Pat. Nos. 6,225,042, 6,355,479, and 6,362,001.

In one embodiment, aAPCs are also subjected to a freeze-thaw cycle. In an exemplary freeze-thaw cycle, the aAPCs may be frozen by contacting a suitable receptacle containing the aAPCs with an appropriate amount of liquid nitrogen, solid carbon dioxide (i.e., dry ice), or similar low-temperature material, such that freezing occurs rapidly. The frozen aAPCs are then thawed, either by removal of the aAPCs from the low-temperature material and exposure to ambient room temperature conditions, or by a facilitated thawing process in which a lukewarm water bath or warm hand is employed to facilitate a shorter thawing time. Additionally, aAPCs may be frozen and stored for an extended period of time prior to thawing. Frozen aAPCs may also be thawed and then lyophilized before further use. Preferably, preservatives that might detrimentally impact the freeze-thaw procedures, such as dimethyl sulfoxide (DMSO), polyethylene glycols (PEGs), and other preservatives, are absent from media containing aAPCs that undergo the freeze-thaw cycle, or are essentially removed, such as by transfer of aAPCs to media that is essentially devoid of such preservatives.

In other preferred embodiments, xenogenic nucleic acid and nucleic acid endogenous to the aAPCs, may be inactivated by crosslinking, so that essentially no cell growth, replication or expression of nucleic acid occurs after the inactivation. In one embodiment, aAPCs are inactivated at a point subsequent to the expression of exogenous MHC and assisting molecules, presentation of such molecules on the surface of the aAPCs, and loading of presented MHC molecules with selected peptide or peptides. Accordingly, such inactivated and selected peptide loaded aAPCs, while rendered essentially incapable of proliferating or replicating, retain selected peptide presentation function, and preferably also retain naïve T cell activation function. Preferably, the crosslinking also yields aAPCS that are essentially free of contaminating microorganisms, such as bacteria and viruse, without substantially decreasing the antigen-presenting cell function of the aAPCs. Thus crosslinking maintains the important APC functions of aAPCs while helping to alleviate concerns about safety of a cell therapy product developed using the aAPCs. For methods related to crosslinking and aAPCs, see for example, U.S. Patent Application Publication No. 20090017000, which is incorporated herein by reference.

As the aAPCs prepared and inactivated as described above present exogenous empty MHC molecules, a sufficient amount of selected peptide advantageously may be added to the aAPCs such that a high density of selected peptide-MHC complexes on the aAPC surface is achieved, and such that the high density is substantially greater than a density observed with wild type mammalian APCs. Subsequently, a naïve T cell/inactivated aAPC culture may be maintained for as long a time as is appropriate to activate and enrich for a therapeutically effective population of CTL. For example, the naïve T cell/inactivated aAPC culture time duration may be from about one day to about ten days, such as from two to nine days, three to eight days, or four to six days.

In aAPCs of the present invention, MHC molecules are expressed as empty molecules. Such empty molecules are essentially devoid of any bound antigenic peptide or antigenic peptide fragments of such peptides. As such, the aAPCs with empty MHC molecules may be loaded with one or more antigenic peptides comprising peptides selected from the group consisting of: SLVLNLLEL (SEQ ID NO:3), KNPVLLKIL (SEQ ID NO:7), NLLPKLHVV (SEQ ID NO:9), FLLPHPGLQV (SEQ ID NO:10), LLNMPPAHLK (SEQ ID NO:11), TLVDLPGMTKV (SEQ ID NO:13), TLIDLPGITRV (SEQ ID NO:14), LSLDSSLSSLL (SEQ ID NO:17), LLLDVAYGAVQA (SEQ ID NO:22), FLASESLLKGAL (SEQ ID NO:23), LVLNLLE (SEQ ID NO:32), TLVDLPGM (SEQ ID NO:40), IDLPGITR (SEQ ID NO:61), WLTVLFIFRI (SEQ ID NO:66), LVYLGHVIYL (SEQ ID NO:67), FVPEVSFEL (SEQ ID NO:70), and FQMEQIVYC (SEQ ID NO:72), wherein the peptide or peptides occupy antigen binding sites on MHC molecules expressed on the surface of aAPCs, which binding sites were devoid of bound peptides prior to exposure to the selected one or more antigenic peptides. Once loaded, the selected one or more antigenic peptides are capable of being presented to naïve T cells in a manner that elicits activation of the naïve T cells.

In embodiments in which one peptide species is selected from the group consisting of: SLVLNLLEL (SEQ ID NO:3), KNPVLLKIL (SEQ ID NO:7), NLLPKLHVV (SEQ ID NO:9), FLLPHPGLQV (SEQ ID NO:10), LLNMPPAHLK (SEQ ID NO:11), TLVDLPGMTKV (SEQ ID NO:13), TLIDLPGITRV (SEQ ID NO:14), LSLDSSLSSLL (SEQ ID NO:17), LLLDVAYGAVQA (SEQ ID NO:22), FLASESLLKGAL (SEQ ID NO:23), LVLNLLE (SEQ ID NO:32), TLVDLPGM (SEQ ID NO:40), IDLPGITR (SEQ ID NO:61), WLTVLFIFRI (SEQ ID NO:66), LVYLGHVIYL (SEQ ID NO:67), FVPEVSFEL (SEQ ID NO:70), and FQMEQIVYC (SEQ ID NO:72), that selected peptide species comprises a plurality of peptide molecules, each of which is identical to the other in amino acid composition and sequence. In embodiments in which two or more peptide species are selected from the group consisting of: SLVLNLLEL (SEQ ID NO:3), KNPVLLKIL (SEQ ID NO:7), NLLPKLHVV (SEQ ID NO:9), FLLPHPGLQV (SEQ ID NO:10), LLNMPPAHLK (SEQ ID NO:11), TLVDLPGMTKV (SEQ ID NO:13), TLIDLPGITRV (SEQ ID NO:14), LSLDSSLSSLL (SEQ ID NO:17), LLLDVAYGAVQA (SEQ ID NO:22), FLASESLLKGAL (SEQ ID NO:23), LVLNLLE (SEQ ID NO:32), FLASESLLKGAL (SEQ ID NO:23), LVLNLLE (SEQ ID NO:32), TLVDLPGM (SEQ ID NO:40), IDLPGITR (SEQ ID NO:61), WLTVLFIFRI (SEQ ID NO:66), LVYLGHVIYL (SEQ ID NO:67), FVPEVSFEL (SEQ ID NO:70), and FQMEQIVYC (SEQ ID NO:72), each of the two or more selected peptide species independently comprises a plurality of peptide molecules, each of which is identical to the other in amino acid composition and sequence. These two or more species are each used to contact the aAPCs, either simultaneously or at distinct instances. In each of these embodiments, multi-antigenic or multi-immunogenic MHC-peptide complexes are produced on the aAPCs. Selected peptide loading onto empty MHC molecules preferably occurs under conditions that approximate biological binding conditions, which may be approximated in vitro, ex vivo, or in vivo.

In still other embodiments, aAPCs may be loaded with one or more antigenic peptides comprising peptides selected from the group consisting of: SLVLNLLEL (SEQ ID NO:3), KNPVLLKIL (SEQ ID NO:7), NLLPKLHVV (SEQ ID NO:9), FLLPHPGLQV (SEQ ID NO:10), LLNMPPAHLK (SEQ ID NO:11), TLVDLPGMTKV (SEQ ID NO:13), TLIDLPGITRV (SEQ ID NO:14), LSLDSSLSSLL (SEQ ID NO:17), LLLDVAYGAVQA (SEQ ID NO:22), FLASESLLKGAL (SEQ ID NO:23), LVLNLLE (SEQ ID NO:32), TLVDLPGM (SEQ ID NO:40), IDLPGITR (SEQ ID NO:61), WLTVLFIFRI (SEQ ID NO:66), LVYLGHVIYL (SEQ ID NO:67), FVPEVSFEL (SEQ ID NO:70), and FQMEQIVYC (SEQ ID NO:72), and one or more other antigenic peptides. For exemplary other antigenic peptides, see, e.g., U.S. Pat. No. 7,402,314 and U.S. Patent Application Publication No. 2009/0017000.

Cytotoxic T Lymphocytes (CTL)

The present invention further relates to methods for producing activated T lymphocytes ex vivo to be used as therapeutic compositions and cell therapy products for administration to a patient. To produce activated T lymphocytes ex vivo, naïve T cells are obtained from a pheresis sample withdrawn from a subject and are contacted with aAPCs that have been loaded with selected one or more antigenic peptides of the present invention. As a result, the contacted naïve T cells become activated, in that they are primed to "target cells" expressing at least one epitope that corresponds to selected one or more antigenic peptides with which the naïve T cells were activated. When encountered by the activated T cells, such target cells may be killed by the activated T cells by virtue the ability of the activated T cells to exhibit specific target cell cytotoxicity (i.e., specific cell killing). Thus the activated T cells become Cytotoxic T lymphocytes (CTL). There are many examples in that art for assays that can be used to measure CTL activity for activated T lymphocytes, for example CTL activity can be measured with a standard chromium ($^{51}$Cr) release assay (Brunner et al., *Immunology*. 1968 February; 14(2):181-96).

A pheresis sample comprising naïve T cells may be obtained from a subject that is in need of treatment. Preferably, the subject is a human patient in need of treatment for a cancer. More preferably, the subject is a human patient in need of treatment for multiple myeloma. Alternatively, in appropriate circumstances, immune cells such as naïve T cells may be used that are not derived from a subject to be treated, but which are derived from another compatible source such as a healthy individual as an immune cell donor (Sadovnikova et al., *Eur J Immunol*. 28(1):193-200 (1998); Münz et al., *J Immunol*. 162(1):25-34 (1999); Lu et al., *Can-* cer Immunol Immunother. 58(4):629-38 (2009)). An immortalized or transformed immune cell line may also be employed to prepare activated T cells for use as therapeutic compositions and cell therapy products in accordance with the invention.

The pheresis sample may be collected from the subject by any of a number of suitable lymphocytapheresis, lymphapheresis, and leukaphoresis procedures now known or that become available in the art, which provide for the collection of PBLs from collected peripheral blood, and from which leukocytes may be separated from other plasma components of the sample. Exemplary procedures are illustrated in, e.g., U.S. Pat. Nos. 4,690,915, 5,126,132, 6,255,073, 5,846,827, 6,251,385, 6,194,207, 5,443,983, 6,040,177, and 5,766,920; and U.S. Patent Application Publication Nos. 2009/0010950 and 2007/0258959.

Naïve T cells may be identified experimentally based on one or more appropriate characteristics routinely selected, such as those associated with cell growth and proliferation status, cell phenotype, and cellular activity. With respect to cell growth and proliferation status, naïve T cells preferably comprise a population of resting T cells, that is, they tend to reside in the $G_0$ portion of the cell cycle. Activated T cells are often in $G_1$ or S phase of the cell cycle. Memory T cells comprise T cells that were once naïve but have been activated and have subsequently re-entered a resting state, or comprise naïve T cells that acquired a memory phenotype as a result of homeostatic expansion (see, e.g., Opferman et al., *Science*, Vol. 283, pp. 1745-1748 (1999); Wherry et al., *Nat. Immunol.*, Vol. 4, pp. 225-234 (2003); Kaech et al., *Cell*, Vol. 111, pp. 837-851 (2002); Kieper et al., *Proc. Natl. Acad. Sci. USA*, Vol. 96, pp. 13306-13311 (1999); Goldrath et al., *J. Exp. Med.*, Vol. 192, pp. 557-564 (2000); Murali-Krishna et al., *J. Immunol.*, Vol. 165, pp. 1733-1737 (2000)). Such memory T cells may be re-activated upon, for example, re-exposure to priming antigen, assistance from CD4+ T helper cells, and/or exposure to appropriate cytokines. Thus, compared to memory T cells and activated T, naïve T cells are relatively non-proliferative in vivo, unless depletion of the naïve T cell pool (such as occurs during a robust activation of T cells in response to antigen) necessitates a period of relatively slow homeostatic proliferation in order to replenish naïve T cell numbers (see, e.g., Kieper et al., *J. Immunol.*, Vol. 174, pp. 3157-3163 (2005), and Baccala et al., *J. Immunol.*, Vol. 174, pp. 4606-4612 (2005)). With respect to phenotype, naïve T cells may be distinguished from non-naïve T cells (e.g., CD4+ helper T cells, memory T cells, and effector T cells (e.g., CTL)) by the existence and relative level of expression of a naïve T cell-associated CD molecule profile, which may include $CD11a^{low}/LFA-1^{low}$ (or $^{dim}$), $CD25^{low}$, $CD27^+$ (or $^{hi}$), $CD44^{low}$ or $CD44^{int}$, $CD45RA^+$ (or $^{pos}$), $CD45RO^-$ (or $^{neg}$), $CD95^{low}$ (or $^{dim}$), $CD57^-$ (or $^{neg}$), and $CD62L^{hi}$ (or $^{bright}$) as compared to the level of expression observed for non-naïve T cells. Naïve T cells may also be distinguished by a relatively high level of expression of the chemokine receptor, CCR7 ($CCR7^{hi}$) as compared to the level of expression observed for non-naïve T cells (see, e.g., McFarland et al., *PNAS*, Vol. 97(8), pp. 4215-4220 (2000); Ishimaru et al., *Nature Immunol.*, Vol. 7(7), pp. 763-772 (2006); and Kern et al., *Eur. J. Immunol.*, Vol. 29, pp. 2908-2915 (1999)). In contrast, memory cells, for example, may be characterized by a $CD27^{low}$, $CD44^{hi}$, $CD45RA^-$, $CD45RO^+$, $CD57^+$ (or hi), $CD62L^{low}$, and/or $CCR7^{low}$ phenotype (see, e.g., Kern et al., *Eur. J. Immunol.*, Vol. 29, pp. 2908-2915 (1999), and Baccala et al., *J. Immunol.*, Vol. 174:4606-4612 (2005)). With respect to cellular activity, naïve T cells may be characterized by an inability to efficiently produce or secrete interferon alpha, interferon gamma, interleukin (IL)1, IL-2, IL-3, IL-4, IL-5, IL-6, IL-7, IL-8, IL-9, IL-10, IL-12, tumor necrosis factor alpha (TNF-α), and/or granulocyte macrophage-colony stimulating factor GM-CSF (see, e.g., Cerwenka et al., *J. Immunol.*, Vol., 161, pp. 97-105 (1998); Walzer et al., *Cell. Immunol.*, Vol. 206, pp. 16-25 (2000); U.S. Patent Application Publication No. 2002/0119121. Naïve T cells also do not exhibit substantive cytotoxicity or specific cell killing activity towards presumptive target cells.

Preferably, these naïve T cells, which may be naïve CD4+ T cells, naïve CD8+ T cells, or naïve CD4+ T cells and naïve CD8+ T cells, are substantially separated from other peripheral blood leukocytes (PBLs), e.g., non-T cells, and then employed to produce a therapeutic composition or a cell therapy product containing activated T cells. Methods for selection of PBLs include procedures employing Ficoll gradients, techniques employing immunopurification (e.g., monoclonal antibodies directed against cell surface markers, such as CD molecules, and beads, such as Sepharose-, Protein A-, and Protein G-conjugated beads to which the antibodies may be adsorbed, and magnetic beads to which antibodies may be adsorbed), flow cytometry, and fluorescence-activated cell sorter (FACS) analysis. Preferably, selected naïve T cells are substantially purified by magnetic bead purification systems such as those available in the art, e.g., Miltenyi beads (Myltenyi Biotec) and Dynabead systems (Dynal Biotech) combined with cell sorting procedures, such as FACS-based methods, or other appropriate cell sorting devices and methodologies. Substantially purified naïve T cells are then admixed and incubated with selected peptide loaded aAPCs for a time sufficient to activate and enrich for a desired population of activated T cells, such as activated helper T cells, and preferably, CTL or CD8+ memory T cells. Such activated T cells preferably are activated in a peptide-specific manner.

The ratio of substantially separated naïve T cells to aAPCs may also be optimized for the particular individual, e.g., in light of individual characteristics such as the amenability of the individual's lymphocytes to culturing conditions and the nature and severity of the disease or other condition being treated. An exemplary separated naïve T cell to inactivated aAPC ratio is from about 30:1 to 300:1. For example, $3 \times 10^7$ human naïve T cells and $1 \times 10^6$ aAPCs may be admixed and maintained in medium comprising RPMI 1640 culture medium.

Activated T cells, which may comprise naïve CD8+ T cells, naïve CD4+ T cells, or combinations of CD8+ T cells and CD4+ T cells that are primed and stimulated, and therefore activated, as described above, may optionally be restimulated and/or expanded to produce therapeutic compositions and cell therapy products comprising activated T cells of a desired phenotype and number. Exemplary restimulating procedures include adding one or more selected cytokines that promote activated T cell growth, proliferation, and/or differentiation and incubating activated T cells with selected peptide-loaded nonCD8+ cells, such as CD14+ cells. The selection of appropriate cytokines will depend on the desired phenotype of the activated T cells that will ultimately comprise the therapeutic composition or cell therapy product. Thus, naïve CD4+ T cells may be activated and optionally restimulated and/or expanded to become CD4+ T helper (Th) cells, for example CD4+ Th1 cells or CD4+ Th2 cells, and naïve CD8+ T cells may be activated and optionally restimulated and/or expanded to become CTL possessing a T cytotoxic (Tc) like phenotype, for example CTL possessing a Tc1-like phenotype, CTL possessing a Tc2-like phenotype, memory T cells, or a combination of such, as desired by the artisan considering guidance in the art (see, e.g., Cerwenka et al., *J. Immunol.*, Vol. 163(10), pp. 5535-5543 (1999); Mosmann et al., *Immunol. Today*, Vol. 17(3), pp. 138-146 (1996); Carter et al., *Curr. Opin. Immunol.*, Vol. 8(3), pp. 336-342 (1996); Croft et al., *J. Exp. Med.*, Vol. 180, pp. 1715-1728 (1994); Fujihashi et al., *Proc. Natl. Acad. Sci. USA*, Vol. 93, pp. 3613-3618 (1996); and U.S. Pat. No. 6,355,479). Exemplary cytokines include IL-1, IL-2, IL-7, IL-4, IL-5, IL-6, IL-12, IFN-γ, and TNF-α. An exemplary T cell expansion procedure includes incubating activated T cells with irradiated nonCD8+ cells in the presence of selected cytokines and an anti-CD3 antibody preparation, such as OKT®3, to promote non-specific activated T cell expansion. Selection of the number, sequence, and combination of such restimulating and expansion protocols to be employed are within the purview of the artisan and may be facilitated by guidance in the art. See, e.g., Cerwenka et al., *J. Immunol.*, Vol. 161, pp. 97-105 (1998); Livingston et al., *Immunol. Invest.*, Vol. 24(4), pp. 619-629 (1995); and Sad et al., *Immunity*, Vol. 2, pp. 271-279 (1995).

In preferred embodiments, T cells that have been stimulated are subsequently subjected to at least one iteration of a restimulating procedure, comprising contacting the stimulated T cells with amounts of IL-2 and IL-7 sufficient to promote the growth, proliferation, and/or differentiation of the activated T cells, and then incubating the so-contacted T cells with irradiated, autologous, adherent nonCD8+ cells (e.g., CD14+ cells) and additional sufficient amounts of IL-2 and IL-7. In embodiments in which the restimulating procedure is performed more than once, the activated T cells are contacted with additional amounts of IL-2 and IL-7 between each iteration of the restimulating procedure. In other preferred embodiments, the activated T cells are subjected to at least one expansion procedure subsequent to the at least one iteration of a restimulating procedure, wherein the expansion procedure comprises incubating activated T cells with irradiated nonCD8+ cells in the presence of an amount of IL-2 sufficient to promote the growth, proliferation, and/or differentiation of the so-contacted T cells, and an anti-CD3 antibody preparation, preferably OKT®3.

In preferred embodiments, the naïve T-cells comprise CD8+ T cells, which when activated and optionally re-stimulated and/or expanded, may exhibit, for example, cytotoxic activity toward cells to which they are targeted or produce immunostimlatory or cytotoxicity-associated cytokines. Preferably, they exhibit a combination of these features. Naïve CD8+ T cells that have been primed and activated may be subjected to restimulating procedures and/or expansion protocols as described above, which drive differentiation of activated CD8+ T cells toward specific CTL cell lineage phenotypes. The peptide-loaded aAPC-activated CD8+ T cells may also be subjected to several rounds of the restimulating procedure, in vivo or in vitro, with selected peptide alone or in conjunction with certain cytokines, such as IL-2, IL-7, and IL-12, and interferon gamma or with antibodies, such as those directed against the T cell receptor (TCR) and costimulatory molecules on the surface of the activated T cells. In preferred embodiments, activated CD8+ T cells are further restimulated in this way, which maintain immunogenicity and cytotoxicity for target cells for at least about four or five generations, yielding memory CD8+ T cells. Methods for memory CD8+ T cell identification, characterization, immunogenicity maintenance, and expansion may be found in, for example, Cerwenka et al., *J. Immunol.*, Vol., 161, pp. 97-105 (1998); Cerwenka et al., J. Immunol., Vol. 163, pp. 5535-5543 (1999); U.S. Patent Application Publication No. 2002/0119121.

Activated T cells may be separated from the aAPCs using a suitable technique known or available in the art. For example, monoclonal antibodies specific for the aAPCs, for the peptides loaded onto the aAPCs, or for the activated T cells (or a portions thereof) may be employed to bind an appropriate complementary ligand. Antibody-tagged cells may then be extracted from the aAPC/activated T cell admixture by a suitable technique, such as an immunoprecipitation or immunoassay method. Alternatively, a separation step may be omitted completely and the inactivated aAPCs may be left in culture with the activated T cells.

In a preferred embodiment, naïve CD8+ T cells are selected for activation, and desired amounts of resulting CTL are employed to prepare a cell therapy product for therapeutic administration. Preferably, prior to administration one or more quality assurance tests are performed on the activated T lymphocytes or cell therapy product. In preferred embodiments, the quality assurance testing comprises performing one or more tests to confirm: HLA match between patient and T lymphocytes; flow cytometry analysis (CD8+, TCR+); sterility (no bacterial or fungal growth); gram-stain negative for bacteria; mycoplasma negative for PCR/ELISA; no residual *Drosophila* DNA; absence of insect virus cDNA; viability (>72% viable); and cytolytic activity by CTL assay.

To treat a subject, an effective amount of a cell therapy product according to the present invention is administered to a subject suffering from or diagnosed as having a disease, disorder, or condition. An "effective amount" is an amount or dose sufficient to generally bring about a desired therapeutic or prophylactic benefit in patients in need of such treatment. Effective amounts or doses of the cell therapy products of the present invention may be ascertained by routine methods such as modeling, dose escalation studies or clinical trials, and by taking into consideration routine factors, e.g., the mode or route of administration or product delivery, the pharmacokinetics of the cell therapy product, the severity and course of the disease, disorder, or condition, the subject's previous or ongoing therapy, the subject's health status and response to drugs, and the judgment of a treating physician. As exemplary dosage amounts, cell populations may comprise from about $1 \times 10^6$ to about $1 \times 10^{12}$ activated T cells, such as $1 \times 10^8$ to $1 \times 10^{11}$ or $1 \times 10^9$ to $1 \times 10^{10}$ activated T cells for an adult human.

The cell therapy product is prepared as a therapeutic composition comprising activated T cells and a vehicle suitable for the maintenance of the activated T cells until they are infused into the subject, such as a pharmaceutically acceptable diluent or solvent. In a preferred embodiment, the cell therapy product comprises from about $1 \times 10^9$ to about $10 \times 10^9$ CTL in a solution comprising Lactated Ringer's Injection Solution, USP (76% (v/v), 5% dextrose normal saline (D5NS; 4% (v/v)), and 25% human serum albumin (HSA; 20% (v/v)).

Any suitable technique for administering compositions comprising cellular components into a subject may be employed. For example, administration of activated CTL via intravenous infusion may be employed. Multiple infusions may be required or indicated, and these infusions may occur over a period of several weeks or longer. Exemplary techniques are described in, for example, U.S. Pat. Nos. 4,844,893 and 4,690,915.

Optionally, the cell therapy products or preparations may be supplemented to include other immunomodulatory, preferably immunostimulatory, components in addition to selected peptide-loaded aAPCs. Such additional components may be added prior to, concomitant with, or subsequent to contacting naïve T cells with the peptide-loaded aAPCs. The selection of desired time points and dosage concentrations and frequencies at which such supplemental immunomodulatory, preferably immunostimulatory, components are added may be selected according to relevant considerations, such as desired proliferation rate, expansion rate, cell number, longevity, or immunogenicity. Supplemental or immunostimulatory components may be, for example, one or more leukocytes other than non-naïve T cells, cytokines, lymphokines, chemokines, and antibodies. Exemplary leukocytes that may be selected include adherent cells, such as non-CD8 adherent cells, CD14+ adherent cells, monocytes, macrophages, helper T cells, memory T cells, and other leukocytes that may impart an immunomodulatory, preferably immunostimulatory, effect or stimulus. Such leukocytes may be of autologous or heterologous origin. Exemplary cytokines include interleukins, such as IL-1, IL-2, IL-3, IL-4, IL-5, IL-6, IL-7, IL-8, IL-9, IL-11, IL-12, IL-15, IL-17, IL-21, interferons, such as g-interferon, and tumor necrosis factors (TNFs), such as TNF-α (see, e.g., Tizard I., *Immunology: An Introduction*, 3rd Edition, pp. 129-143, (1992); U.S. Patent Application Publication No. 2002/0119121). The cytokines may be of recombinant or natural origin. Exemplary antibodies include monoclonal anti-CD3 antibodies, such as that marked as ORTHOCLONE OKT®3 (muromonab-CD3).

In one embodiment of the present invention, autologous non-CD8, CD14+ adherent cells, IL-2, IL-7, and monoclonal anti-CD3 antibody preparation (OKT®3) are employed as additional immunostimulatory components in cell therapy preparation methods. In such embodiments, naïve T cells that have been subjected to primary stimulation with selected peptide-loaded aAPCs are subjected to a restimulating procedure comprising contacting them with effective amounts of recombinant IL-2 and recombinant IL-7 (e.g., about 1-100 Units/ml IL-2 and preferably 1, 10, 15, 20, 50 or 100 Units/ml IL-2 and about 1-100 Units/ml IL-7, and preferably 1, 10, 15, 20, or 50 Units/ml IL-7), and then contacting them with an effective amount of autologous, selected peptide-loaded, non-CD8, CD14+ adherent cells (e.g., about one non-CD8, CD14+ adherent cell for every four primary-stimulated naïve T cells). The time duration of the IL-2/IL-7 and CD14+ adherent cell contact is about two days and from about three to about four days, respectively, and each restimulating procedure may be repeated in sequence at least once. After at least two of the restimulating procedures, a non-specific T cell expansion regimen comprises contacting the cells with IL-2 and anti-CD3 (e.g., OKT®3) for about two to about five days.

In other embodiments, autologous CD4+ helper T cells and IL-2, IL-7, IL-12, IL-15, IL-17, or IL-21 are contacted with naïve T cells prior to, concomitant with, or subsequent to primary stimulation or restimulating procedures. IL-2 may also be used in combination with at least one of IL-7, IL-15 or IL-21. Where IL-15 is used, effective amounts of IL-15 are about 1-100 ng/ml, for example amounts of 1, 10, 20, 25, 40, or 50 ng/ml IL-15. Similarly, where IL-21 is used, effective amounts of IL-21 are about 1-100 ng/ml, for example 1, 10, 20, 25, 40, or 50 ng/ml IL-21. In such embodiments, naïve CD4+ helper T cells may be directed to become memory T cells. Such a CD4+ helper T cell regimen may be employed in addition to or in lieu of any of the restimulating procedures or non-specific T cell expansion procedures described above, rendering memory T cells that may tolerate multiple rounds of the restimulating procedures ex vivo. Additionally, a cell therapy product comprising such memory T cells, when administered to a subject, may then be expanded and stimulated in vivo when encountered with selected peptide and other activating cues. Processes generally relating to the preparation of helper T cells and their incorporation into IL-2, IL-7, IL-12, IL-15, IL-17, and/or IL-21 assisted stimulation or expansion of naïve T cells to become memory T cells or CTLs may be found in, e.g., U.S. Patent Application Publication No. 2002/0119121.

In order to treat a subject, a cell therapy product is preferably administered to the subject from whom the pheresis product used to prepare the cell therapy product was originally obtained. Therefore, a subject who is treated with a cell therapy product is preferably administered a cell therapy product that comprises autologous activated T cells, and more preferably that comprises CTL. Activated T cells can be reinfused or transfused back into the subject from whom the pheresis sample used to derive the activated T cells was obtained. Reinfusion procedures that may be employed include those procedures disclosed in, for example, U.S. Pat. Nos. 4,844,893 and 4,690,915.

Exemplary diseases, disorders, or conditions that may be treated with a cell therapy product in accordance with the invention include, for example, cancers such as multiple myeloma. Treatment of a disease, disorder, or condition with a cell therapy product in accordance with the invention may occur before, concomitant with, or after other treatment with other therapeutic products or regimens. Exemplary additional regimens, components, or modalities that may be used in conjunction with administration of the inventive cell therapy product include, for example: immunostimulatory, immunosuppressive and other immunotherapy regimens, such as cytokine, lymphokine, chemokine, interleukin, or interferon administration; lymphodepleting and myeloblative regimens, such as denileukin diftitox (DAB-IL2) or cladribine administration; and traditional chemotherapy and radiation treatments. In a preferred embodiment, a lymphodepleting treatment regimen, such as that disclosed in International Publication No. WO 2007/103009, is employed in conjunction with treatment with the cell therapy product.

Accordingly, naïve T cells advantageously may be obtained from a subject suffering from a condition or disease treatable with the inventive cell therapy product prior to the initiation of another treatment or therapy that may interfere with, attenuate, or limit the activation of the naïve T cells. For example, in the treatment of an individual with a neoplasia or tumor, a lympapheresis product comprising naïve T cells may be obtained prior to the initiation of chemotherapy or radiation treatment and kept in culture or frozen for later use. The naïve T cells may then activated in accordance with the present invention, thereby providing a cell therapy product, which may be infused into the subject prior to, concomitant with, or after other treatment regimens.

Other embodiments, features, and advantages of the invention are further illustrated by reference to the following examples.

EXAMPLES

Without further description, it is believed that one of ordinary skill in the art can, using the preceding description and the following illustrative examples, make and utilize the present invention and practice the claimed methods. The following working examples therefore, specifically point out embodiments of the present invention, and are not to be construed as limiting in any way the remainder of the disclosure.

Cell Culture of U266 Cell Line

The cell line used for antigen identification, U266 (ATCC No. TIB-196), was expanded in cell culture flasks and stir bottles in supplemented RPMI medium (Invitrogen), with 10% Fetal Calf Serum (FCS) (Invitrogen). On day 1, cells were usually seeded at $0.5 \times 10^6$ cells/ml and cells were split when the cell density reached to $2 \times 10^6$ cells/ml, typically on day 3 or day 4.

Cell Harvest for U266 Cell Line

The cultured cells were collected by centrifugation of cell suspension at 4000 rpm for 20 minutes and washed three times with ice-cold 1× phosphate buffered saline (PBS) (Invitrogen) in 50 ml conical tubes and then counted. Aliquots of cell pellets corresponding to approximately $1 \times 10^9$ cells were snap-frozen in liquid nitrogen and stored at −80° C. until use.

Conjugation of HLA-A2 Antibody to Dynabeads®

The BB7.2 HLA-A2 antibody was purified from cell culture supernatant of hybridoma cell line ATCC® Number: HB-82™ (Parham and Brodsky, Hum Immunol. 3(4):277-99 (1981)). The BB7.2 antibody is also available from Santa Cruz Biotechnology, Inc. (Product # sc-32236) and Abcam (Product # ab74674). The BB7.2 antibody is a mouse monoclonal anti-HLA-A2 antibody and it is an $IgG_{2b}$ isotype. The antibody recognizes an epitope at the C-terminus of alpha-2 helix and a turn on one of the underlying beta strands within the human HLA-A2 histocompatibility antigen. BB7.2 will recognize all HLA-A2 subtypes. HLA-A2.1 represents 90% of the A2 subtypes, the remaining 10% include primarily, A2.2, A2.3, A2.5 and A2.7. Prior to conjugation of the BB7.2 HLA-A2 antibody, 0.5 ml of Dynabeads® MyOne™ Tosylactivated beads (Dynal® Biotech, Cat. No. 655.01) were collected and washed 4 times with coating buffer, which contained 0.1M sodium borate buffer pH9.5. Beads were then incubated with 0.42 ml of 4.8 mg/ml BB7.2 HLA-A2 antibody, 2.08 ml of 3M $(NH_4)_2SO_4$ in 3.26 ml of coating buffer at room temperature (RT) for 72 hours. Supernatant was removed by Dynal® MPC™-1 magnetic particle concentrator (Dynal Biotech ASA, OSLO, Norway) The same total volume of PBS with 0.5% bovine serum albumin (BSA) and 0.05% Tween 20 was then added to the beads and the beads were incubated at RT for another 48 hours. Beads were then washed three times with PBS with 0.1% BSA and 0.05% Tween 20, and resuspend in 2 ml PBS with 0.02% sodium azide.

The efficiency of BB7.2 HLA-A2 antibody conjugation was evaluated by comparing the amount of BB7.2 HLA-A2 antibody in solution before and after conjugation to the Dynabeads® MyOne™ Tosylactivated beads. Samples containing 2 ug of total protein were added to sample buffer and boiled at 100° C. for 15 minutes. Samples were analyzed by 10-20% SDS-PAGE (Data not shown). Conjugation was determined to be more than 90%.

Isolation of HLA-A2-associated Peptides

Aliquots of U266 cell pellets (from $1 \times 10^9$ cells) were resuspended at $2.5 \times 10^7$ cells/ml in 40 ml of lysis buffer containing 50 mM Tris (pH8.0), 150 mM NaCl, 1% CHAPS (Aldrich, Cat. No. 226947), 5 uM EDTA, 0.2% sodium azide, 17.4 µg/ml PMSF (Calbiochem-Novabiochem) and 2 tablets of Complete Proteases Inhibitor Cocktail Tablets (Roche, Cat. No. 1697498) for 1 hour at 4° C. using a rotator. The lysates were centrifuged at 100,000×g, for 1 hour. The pellets were discarded and the supernatant passed through a 0.22-µm filter. The supernatant was then incubated with BB7.2 HLA-A2 antibody-conjugated Dynabeads® (1 mg BB7.2 HLA-A2 antibody/25 mg Dynabeads®) at 4° C. for 24 hours using a rotator). The bead pellets were collected by using the Dynal® MPC™-1 and washed with a series of 50 ml washes with the following 4 different wash buffers.

Wash buffer 1: 50 mM Tris (pH8.0), 150 mM NaCl, 0.05% CHAPS, 5 uM EDTA, 0.2% sodium azide, 17.4 µg/ml PMSF Wash buffer 2: 50 mM Tris (pH8.0), 150 mM NaCl Wash buffer 3: 50 mM Tris (pH8.0), 450 mM NaCl Wash buffer 4: 50 mM Tris (pH8.0)

After the series of 4 wash steps, the beads were incubated with 2 ml of 10% HAC (pH2.5) at RT for 5 minutes and peptides were eluted from BB7.2 HLA-A2 antibody-conjugated Dynabeads® by using the Dynal® MPC™-1 for 5 minutes. Material eluted from the beads was placed in 1.5 ml Eppendorf plastic tubes and boiled for 5 minutes to further dissociate any bound peptide from the MHC class I, HLA-A2, heavy chains. The peptides were then separated from the co-purifying heavy chains and B2-microglobulin by centrifugation using an Ultrafree-CL membrane with a nominal molecular weight cut-off of 5000 Daltons (Amicon, Cat. No. UFC4LCC25, Millipore Corporation, Bedford, Mass.). Prior to use, Ultrafree-CL membrane units were prewetted with 1 ml of 10% acetic acid, spun for 1 hour, and all liquid in both reservoirs was discarded. Material eluted from the beads was then transferred to the prewetted Ultrafree-CL membrane units which were centrifuged at 3500×g for approximately 5 hours at 4° C. Both the filtrate and retentate were collected. Aliquots of peptide-free fractions containing MHC class I, HLA-A2 molecules (retentate) were analyzed by SDS-PAGE. Peptide free fractions were 95% pure with expected bands of 44 kDa and 12 kDa for MHC class I heavy chains and β2-microglobulin, respectively (Data not shown). Peptide solutions (filtrate) were analyzed by liquid chromatography tandem mass spectrometry (LC/MS/MS) and subsequently the amino acid sequences of the peptides were determined by de novo peptide sequencing.

Liquid Chromatography Tandem Mass Spectrometry (LC/MS/MS)

Peptide solutions (filtrate from isolation of HLA-A2-associated peptides) were acidified by adding 1% trifluoroacetic acid (TFA). For each sample, 10 ul was injected into an Eksigent nanoLC (Eksigent Technologies, Inc.) for desalting/trapping and analysis with the following setup: Trapping column=LC Packings C18 Pepmap 100, 5 u, 100 A, 300 um id×5 mm; Trapping mobile phase=water, 2% methanol, 0.05% TFA; Trapping flow rate=5 uL/min; Analysis column=Vydac Everest C18, 5 u, 300 A, 75 um id×150 mm; Analysis mobile phases: A=water, 2% methanol, 0.1% formic acid; B=10% water, 90% acetonitrile, 0.1% formic acid; Flow rate=0.2 uL/min. Analysis gradient=0-80 min 10-30% B, 80-120 min 30-60% B. Data-dependent MS/MS acquisition was carried out on a Micromass qTOF Ultima with Masslynx 4.0 and nanoSource in ESI+ mode. ProteinLynx 2.0 was employed for de novo peptide sequencing.

Sequence Determination of Antigenic Peptides

Peptide sequences derived from de novo sequencing using LC/MS/MS are usually ambiguous due to incomplete peptide fragmentation. When a peptide collides with Argon gas, not every possible fragment is necessarily generated. In fact, some peptide bonds may always stay intact. In addition, not every peptide fragment may be detected by mass spectrometer due to a variety of reasons (e.g., co-eluting, ion suppression, or the fragment may not carry a positive charge). Thus LC/MS/MS spectra for a particular peptide may not be complete, i.e., there can be missing steps in a ladder. In the present invention, ambiguity in peptide sequences was reduced by using the ProteinLynx 2.0 sequencing tool and then comparing sequences of LC/MS/MS peaks of similar size that were derived from at least three out of five replicate assays and by comparing peptide sequences with the human protein sequence database. In this way, 24 peptide sequences were selected, with length of 9 to 12 amino acids, for 21 LC/MS/MS peaks. 19 of 24 peptide sequences were mapped to known human full-length proteins (Table 1). Additional computer predicted peptides were then derived from a search for HLA binding motifs among the full-length proteins (Parker et al., *J Immunol.* 1992 Dec. 1; 149(11):3580-7). 24 experimentally identified peptides, truncations of some of the peptides, and the computer predicted peptides were synthesized (Prolmmune Inc., Bradenton, Fla.), tested in an HLA-A2 Stabilization Assay, and CTL were generated and their activities were tested in a standard $^{51}$Cr Release Assay. A schematic representation of the peptide identification process is shown in FIG. 1. Table 1 shows a list of 24 selected peptides that were synthesized for further characterization and the associated protein for each peptide, if identified.

TABLE 1

24 peptides that were sequenced and selected to be synthesized for further characterization for HLA-A2 Stabilization and the CTL Activity. Peptide sequences for which full-length proteins were not identified, have empty cells for gene symbol, protein accession number, and amino acid residue numbers from the full-length protein.

| SEQ ID NO | Peptide No. | Peptide Sequence | Length | Gene Symbol | Protein Accession No. | Amino Acid Residues |
|---|---|---|---|---|---|---|
| 1 | P1 | LLGPRLVLA | 9 | TMED10 | P49755 | 23-31 |
| 2 | P2 | LLPGRTVLV | 9 | TEP1 | A0AUV9 | 673-681 |
| 3 | P3 | SLVLNLLEL | 9 | GJA4 | P35212 | 220-228 |
| 4 | P4 | RSLFLLYAL | 9 | BFAR | Q9NZS9 | 267-275 |
| 5 | P5 | VLIPKLPQL | 9 | ORMDL3 | Q8N138 | 134-142 |
| 6 | P6 | KLLEPVLLL | 9 | RPS16 | Q6IPX4 | 50-58 |
| 7 | P7 | KNPVLLKIL | 9 | RLF | Q13129 | 185-193 |
| 8 | P8 | YLLPAIVHI | 9 | | 1406327A | 128-136 |
| 9 | P9 | NLLPKLHVV | 9 | CLIC5 | Q9NZA1 | 356-364 |
| 10 | P10 | FLLPHPGLQV | 10 | ATL3 | Q6DD88 | 263-272 |
| 11 | P11 | LLNMPPAHLK | 10 | | | |
| 12 | P12 | LLYQGPHNTL | 10 | ITGA4 | P13612 | 48-57 |
| 13 | P13 | TLVDLPGMTKV | 11 | DNM1L | O00429 | 143-153 |
| 14 | P14 | TLIDLPGITRV | 11 | MX1 | P20591 | 175-185 |
| 15 | P15 | ALNEEAGRLLL | 11 | UBE2S | Q16763 | 128-138 |
| 16 | P16 | HSLDNSLSILR | 11 | DPEP2 | Q9H4A9 | 191-201 |
| 17 | P17 | LSLDSSLSSLL | 11 | IL1F10 | AAK01948 | 21-31 |
| 18 | P18 | LKNKLKDLGH | 10 | USO1 | O60763 | 923-932 |
| 19 | P19 | NLKAALENLGAL | 12 | | | |
| 20 | P20 | LLIDDKGTIKL | 11 | CDC2 | P06493 | 134-144 |
| 21 | P21 | LLLDVPTAAVQA | 12 | IF130 | AAA36105 | 26-37 |
| 22 | P22 | LLLDVAYGAVQA | 12 | | | |
| 23 | P23 | FLASESLLKGAL | 12 | | | |
| 24 | P24 | LKIHAREIFD | 10 | ENO1 | P06733 | 4-13 |

HLA-A2 Stabilization Assay

The assay for peptide binding to class I major histocompatibility complex (MHC/HLA-A2) molecules is based on the ability of peptides to stabilize MHC class I, HLA-A2 molecules that are synthesized in a transporter associated with antigen processing (TAP)-deficient cell line, T2 (ATCC® Number: CRL-1992). The extent of stabilization of MHC class I molecules is directly related to the binding affinity of the added peptides (Townsend et al., *Cell.* 1990 Jul. 27; 62(2):285-95; Andersen et al., *Tissue Antigens.* 1999 August; 54(2):185-90).

For the assay, T2 cells were plated in 96-well V-bottom plates, 100 ul/well RPMI media, at a density of 1×10$^6$ cells/ml, with final peptide concentrations of 200 uM, 20 uM, 2 uM, 200 nM, 20 nM, 2 nM, and no peptide as negative control. The cells with peptides were incubated for 18 hours at 26° C., 5% $CO_2$. After 18 hours, the plates were transferred to 37° C., 5% $CO_2$ and incubated for an additional 3 hours. The cells in plate were washed once with FACS buffer (PBS, 2.5% FCS, 1% $NaN_3$) and then stained by adding 1 ul/well FITC-labeled mouse anti-human HLA-A2 antibody (BD Pharmingen, Cat. No. 551285), 1 ul/well PI, and then incubating at 4° C. for 30 minutes. After staining, cells were resuspended in 200 ul of FACS buffer and transferred from 96-well plates to racks of 96 microtubes. Samples were run on a FACScan flow cytometer and the data were analysed by using CellQuest software.

FIG. 2 shows graphs of Median Fluorescence Intensities (MFI) vs. peptide concentrations for the 24 selected peptides that were synthesized and assayed for their ability to bind and stabilize HLA-A2 molecules in T2 cells. A peptide of Hepatitis B Core protein (HBC) was used as a positive control. The Hepatitis B Core peptide is a potent HLA-A2.1 epitope and consists of residue numbers 18-27 of the core sequence, amino acids FLPSDFFPSV (SEQ ID NO:73) (Zhang et al. *Immunology.* 2007, 121(1):105-12). Binding affinity of the peptides was characterized as Strong (S), Median (M), Weak (W), None (N) and is summarized in Table 2.

TABLE 2

Relative binding affinities for 24 selected peptides.
Binding affinities were characterized as Strong (S), Median (M), Weak (W), None (N).

| N | W | M | S |
|---|---|---|---|
| P2 | P1 | P5 | P14 |
| P4 | P3 | P6 | P15 |
| P18 | P7 | P8 | |
| P19 | P9 | P10 | |
| P24 | P11 | P13 | |
| | P12 | P20 | |
| | P16 | P21 | |
| | P17 | | |
| | P22 | | |
| | P23 | | |

Cytotoxic T Lymphocytes (CTL) Generation

Drosophila aAPC were generated from Schneider S2 cells (S2 cells), which were originally established in 1969 from several hundred Oregon-R (wild type) *Drosophila melanogaster* (Oregon-R) embryos (American Type Culture Collection (ATCC) CRL-1963) according to published procedures (Schneider, *J. Embryol. Exp. Morph.* 1972 Vol 27, pp. 353-365), and deposited in the ATCC(CRL10974). S2 cells are grown in commercial Schneider's *Drosophila* medium supplemented with 10% heat-inactivated fetal bovine serum. In order to generate aAPCs, human complementary DNAs (cDNAs) for HLA-A2.1, B7.1, LFA-3, ICAM-1 and CD70, were individually inserted into the pRmHa-3 vector and S2 cells were transfected using the calcium phosphate precipitation method with a mixture of HLA-A2.1, B7.1, LFA-3, ICAM-1 and CD70 plasmid DNAs (for aAPC clone 1120) and the phshneo plasmid. (see U.S. Pat. No. 6,225,042 regarding construction and use of pRMHa plasmid vectors). The human cDNAs were prepared using standard techniques by reverse transcription-PCR using primers derived from the published sequences for HLA-A2.1 from K562 cells, B7.1 from K562 cells, LFA-3 from HL60 cells, ICAM-1 from K562 cells, and CD70 from HLA-A2.1+ LCL cells. K562 cells are a human erythroleukemic cell line, HL60 cells are a promyelocytic leukemia human cell line, and HLA-A2.1+ LCL cells are an Epstein-Barr virus (EBV)-transformed lymphoblastoid cell line (LCL). Stably transfected cells were selected by culturing in Schneider's medium containing geneticin. Prior to scale up of the cells, expression of the transfected genes is induced by the addition of CuSO4. The level of expression is assessed by flow cytometry using anti-HLA-A2.1, anti-B7.1, anti-LFA-3, anti-ICAM-1 and CD70 antibodies. For efficient in vitro activation of the CD8+ lymphocytes, greater than 30% of the *Drosophila* cells must express the HLA-A2.1 molecule. The *Drosophila* cells regularly express each of the molecules at levels between 70-90%. *Drosophila* aAPC were washed and then incubated at RT for 4 hours with 10 µM of different combinations of mixed peptides or individual peptides (See e.g. U.S. Pat. Nos. 6,225,042, 6,355,479, 6,362,001 and 6,790,662; U.S. Patent Application Publication Nos. 2009/0017000 and 2009/0004142; and International Publication No. WO2007/103009). Purified human CD8+ T cells from HLA-A2 positive donors were then incubated with peptide-loaded *Drosophila* APC at 37° C., 5% $CO_2$, for 5 days. Human IL-2 (20 U/ml, R&D Systems) and IL-7 (30 U/ml, R&D Systems) were added at day 5 and the activated CD8+ T cells (CTL) were re-stimulated twice, at day 7 and day 15, with non-CD8 adherent cells in a total peripheral blood mononuclear cell (PBMC) preparation from the same donor in the presence of peptides.

A number of different CTL were generated using CD8+ T cells from different donors and different combinations of mixed peptides, including combinations that contained only one peptide. For example, 24 selected peptides were mixed or used individually to create different combinations of peptide mixtures (PM) or individual peptides (P5 and P14) and produce peptide-loaded *Drosophila* APC. The resulting peptide-loaded *Drosophila* APC were incubated with CD8+ T cells from 2 different donors (Donor 1 and Donor 2) to produce 11 different batches of CTL (Donor 1: PM1, PM2, PM3, PM4, and P14; Donor 2: PM1, PM2, PM3, PM4, P5, and P14) (Table 3).

TABLE 3

Compositions comprising combinations of mixed peptides and compositions that contained only one peptide, that were used to produce 11 different batches of CTL (Donor 1: PM1, PM2, PM3, PM4, and P14; Donor 2: PM1, PM2, PM3, PM4, P5, and P14)

| Donor 1 | PM1 | PM2 | PM3 | PM4 | | P14 |
|---|---|---|---|---|---|---|
| Peptides | 1, 7, 9, 12 | 13, 17, 21 | 5, 6, 8, 10 | 14, 15, 20 | | 14 |
| Donor 2 | PM1 | PM2 | PM3 | PM4 | P5 | P14 |
| Peptides | 5, 6, 8, 10, 13 | 14, 15, 17, 20, 21 | 1, 3, 7, 9, 11 | 12, 16, 22, 23 | 5 | 14 |

Subsequently, three of the peptides (P3, P13, and P14) were used to generate CTL from another HLA-A2 positive donor (Donor 16 FIG. 5) and more CTL were generated with CD8+ T cells from additional HLA-A2 positive donors using combinations of mixed peptides or individual peptides (Table 4).

utes. To start the assay, 100 ul CTL ($5 \times 10^6$ cells/ml starting concentration) were serially diluted 1:5 with MLR medium in a round bottom 96-well plate with duplicates for each effector cell concentration. To each well containing 100 ul of different dilutions of CTL, 50 ul of K-562 cells ($4 \times 10^6$ cells/ml) (ATCC® Number: CCL-243™) and 50 ul of peptide loaded

TABLE 4

Compositions comprising combinations of mixed peptides and compositions that contained only one peptide, that were used to produce CTL from a number of additional HLA-A2 positive donors.

| CTL ID | Effector 1 | Effector 2 | Effector 3 | Effector 4 | Effector 5 | Effector 6 |
|---|---|---|---|---|---|---|
| Donor 1 | PM1(P1, P7, P9, P12) | PM2(P13, P17, P21) | PM3(P5, P6, P8, P10) | PM4(P14, P15, P20) | P14 | |
| Donor 2 | PM1(P5, P6, P8, P13, P14) | PM2(P14, P15, P17, P20, P21) | PM3(P1, P3, P9, P11) | PM4(P12, P16, P22, P23) | P5 | P14 |
| Donor 3 | PM1(P1, P5, P6, P8) | PM2(P13, P17, P20, P21) | PM3(P1, P3, P7, P11) | PM4(P12, P16, P22, P23) | | |
| Donor 4 | PM1(P1, P14, P15, P17) | | | | P14 | |
| Donor 5 | P1 | P3 | P8 | P14 | P15 | P17 |
| Donor 6 | P1 | P14 | P15 | P17 | | |
| Donor 7 | P1 | P14 | P15 | P17 | | |
| Donor 8 | PM1(P1, P14, P15, P17) | PM2(P3, P8, P13) | P14 | P3 | | |
| Donor 9 | PM1(P3, P14, P15, P17) | | | | | |
| Donor 10 | PM1(P1, P14, P15, P17) | PM2(P3, P8, P13) | | | | |
| Donor 11 | PM1(P1, P3, P13, P14) | | | | | |
| Donor 12 | PM1(P3, P13, P14) | | | | | |
| Donor 13 | PM1(P3, P13, P14) | | | | | |
| Donor 14 | PM1(P3, P13, P14) | P14 | | | | |
| Donor 15 | PM1(P3, P13, P14) | P14 | | | | |
| Donor 16 | PM1(P3, P13, P14) | | | | | |
| Donor 17 | PM1(P3, P13, P14) | P14 | | | | |

Chromium ($^{51}$Cr) Release Assay for CTL Activity

CTL (Effector) activity was measured with a standard chromium ($^{51}$Cr) release assay, with T2 cells (Target) loaded with individual peptides and also with a number of tumor cell lines as target cells (Brunner et al., *Immunology*. 1968 February; 14(2):181-96). The highest Effector (E) Target (T) ratio (E/T) was 50:1, with 1:5 serial dilutions of CTL (Effector) used to produce a dose response. Before the assay, Target cells (T2 cells at $3 \times 10^6$ cells/100 ul in 1×PBS with 4% FCS) were labeled by adding 100 ul of $^{51}$Cr (Perkin Elmer) and incubating at 37° C. for 1 hour. After incubation, labeled target cells were washed 4 times with 1× Hank's Balanced Salt Solution (Invitrogen) with 2.5% Horse Serum (Invitrogen), spun at 1200-1500 rpm for 8 minutes at 4° C., and resuspended in 15 ml of fresh MLR media (RPMI-1640 including 10% FCS, 1% Glutamin, 1% penicillin-streptomycin, 1% HEPES and 1% MEM Non-Essential Amino acids solution). The final concentration of labeled T2 cells was $0.2 \times 10^6$ cells/ml. Before the assay, the labeled T2 cells were loaded with 10 uM of individual peptide at R.T. for 30 min- $^{51}$Cr-labeled T2 target cells ($0.2 \times 10^6$ cells/ml) were added. The plate was incubated at 37° C., 5% $CO_2$, for 4 hours, then spun at 900 rpm for 5 minutes, and 100 ul of supernatant from each well was transferred to $^{51}$Cr counting tubes and counted.

Figure 5:
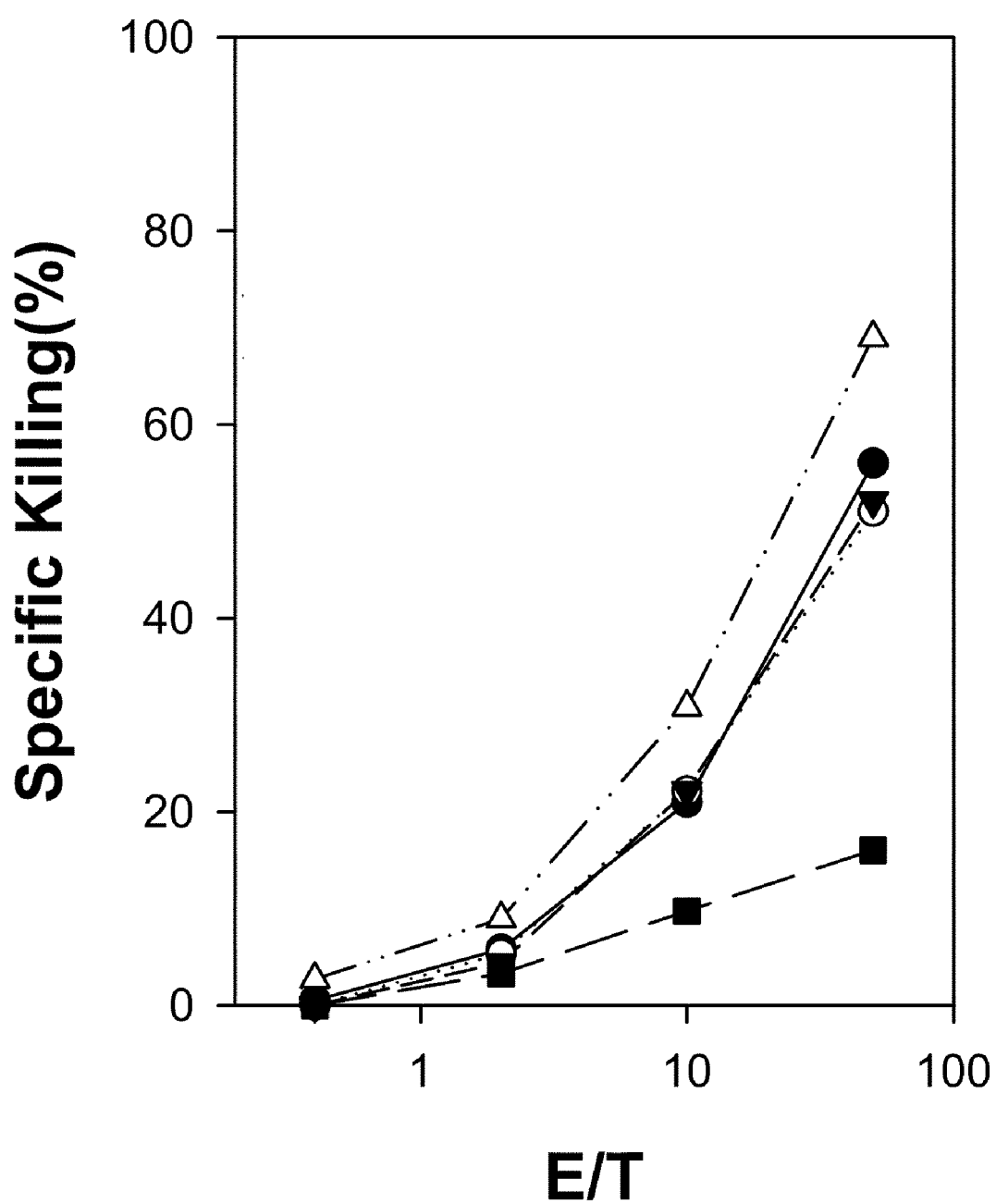
FIG. 5: Shown is a graph of CTL activity measured in the $^{51}$Cr Release Assay. CTL were generated from a single HLA-A2 positive donor (Donor 16), using a mixture (PM) of 3 selected peptides, P3, P13, and P14. CTL activity was measured in the $^{51}$Cr Release Assay with T2 cells loaded with the individual peptides or the same peptide mixture that was used to generate the CTL. Data are shown as Specific Killing (%) vs. Effector (E) Target (T) ratio (E/T). Specific Killing (%) for T2 cells loaded with each peptide or peptide mixture are labeled as follows: P3 (filled circle), P13 (open circle), P14 (closed triangle), PM (open triangle), and no peptide (closed square).

The $^{51}$Cr Release Assay showed that nine peptides (P1, P3, P5, P10, P13, P14, P15, P17, and P23) induced CTL in two normal donors (Donor 1 and Donor 2) (FIG. 3 and FIG. 4, respectively). One combination of three peptides (P3, P13, and P14) was used to generate CTL from another donor (Donor 16) and tested for the ability to kill T2 cells loaded with the individual peptides or a mixture of the peptides (FIG. 5).

The 24 peptides were subsequently used to generate CTL from additional donors and the relative activity for CTL generated from each peptide was characterized as Strong (S), Median (M), Weak (W), None (N), or not determined (n.d.). CTL activity was determined as a ratio of the number of donors that elicited each level of activity over the total number of donors used to generate CTL for each peptide (Table 5).

TABLE 5

CTL activities in $^{51}$Cr Release Assay using T2 cells as target cells loaded with individual peptides. CTL activity was characterized as Strong (S), Median (M), Weak (W), None (N), or not determined (n.d.) and CTL activity was determined as a ratio of the number of donors that elicited each level of activity over the total number of donors used to generate CTL for each peptide.

| SEQ ID NO | Peptide No. | Peptide Sequence | CTL Activities | | | | |
|---|---|---|---|---|---|---|---|
| | | | Strong | Median | Weak | None | n.d. |
| 1 | P1 | LLGPRLVLA | 2/10 | | 2/10 | 6/10 | |
| 2 | P2 | LLPGRTVLV | | | | | n.d. |
| 3 | P3 | SLVLNLLEL | 5/12 | 1/12 | 4/12 | 2/12 | |

TABLE 5-continued

CTL activities in $^{51}$Cr Release Assay using T2 cells as target cells loaded with individual peptides. CTL activity was characterized as Strong (S), Median (M), Weak (W), None (N), or not determined (n.d.) and CTL activity was determined as a ratio of the number of donors that elicited each level of activity over the total number of donors used to generate CTL for each peptide.

| SEQ ID NO | Peptide No. | Peptide Sequence | CTL Activities | | | | |
|---|---|---|---|---|---|---|---|
| | | | Strong | Median | Weak | None | n.d. |
| 4 | P4 | RSLFLLYAL | | | 1/1 | | n.d. |
| 5 | P5 | VLIPKLPQL | | | 1/3 | 2/3 | |
| 6 | P6 | KLLEPVLLL | | | 1/3 | 2/3 | |
| 7 | P7 | KNPVLLKIL | | | 1/3 | 2/3 | |
| 8 | P8 | YLLPAIVHI | | | | 3/3 | |
| 9 | P9 | NLLPKLHVV | | | | 2/2 | |
| 10 | P10 | FLLPHPGLQV | 1/2 | | | 1/2 | |
| 11 | P11 | LLNMPPAHLK | 1/2 | | 1/2 | | |
| 12 | P12 | LLYQGPHNTL | | | 1/3 | 2/3 | |
| 13 | P13 | TLVDLPGMTKV | 4/13 | 2/13 | 5/13 | 2/13 | |
| 14 | P14 | TLIDLPGITRV | 14/17 | 1/17 | 1/17 | 1/17 | |
| 15 | P15 | ALNEEAGRLLL | 3/9 | | 5/9 | 1/9 | |
| 16 | P16 | HSLDNSLSILR | | | | 2/2 | |
| 17 | P17 | LSLDSSLSSLL | 4/10 | | 4/10 | 2/10 | |
| 18 | P18 | LKNKLKDLGH | | | | | n.d. |
| 19 | P19 | NLKAALENLGAL | | | | | n.d. |
| 20 | P20 | LLIDDKGTIKL | | | 1/3 | 2/3 | |
| 21 | P21 | LLLDVPTAAVQA | 1/3 | | | 2/3 | |
| 22 | P22 | LLLDVAYGAVQA | 1/2 | | | 1/2 | |
| 23 | P23 | FLASESLLKGAL | 1/2 | | | 1/2 | |
| 24 | P24 | LKIHAREIFD | | | | | n.d. |

Additional CTL were also produced and tested with truncated versions of the P3, P13, and P14 peptides (Table 6) and with computer predicted peptides (Table 7), derived from a search for HLA binding motifs among the full-length proteins identified original peptide sequences (Parker et al., *J Immunol*. 1992 Dec. 1; 149(11):3580-7). The truncated peptides and the computer predicted peptides were synthesized and tested in the HLA-A2 Stabilization Assay and CTL were generated and tested in the $^{51}$Cr Release Assay. Binding activity in the HLA-A2 Stabilization Assay were characterized as Strong (S), Median (M), Weak (W), None (N), or not determined (n.d.) and CTL activities in the $^{51}$Cr Release Assay were also characterized as Strong (S), Median (M), Weak (W), None (N), or not determined (n.d.). P3 truncated peptide (P3-8) (FIG. 4A), P13 truncated peptide (P13-13) (Table 6B), P14 truncated peptides (P14-14 and P14-15) (Table 6C), and computer predicated peptides (P3-9, P3-11, P13-17, P13-18, and P14-19) (Table 7) were able to induce CTL in normal donors.

TABLE 6

HLA-A2 binding affinities and CTL activities in the $^{51}$Cr Release Assay using T2 cells as target cells loaded with individual peptides for CTL generated with truncated versions of peptides, P3 (A), P13 (B), and P14 (C). HLA-A2 binding affinity and CTL activity were characterized as Strong (S), Median (M), Weak (W), None (N), or not determined (n.d.).

| SEQ ID NO | Peptide No. | Peptide Seq. | HLA-A2 Binding | CTL Activity |
|---|---|---|---|---|
| A | | | | |
| 3 | P3 | SLVLNLLEL | M | M |
| 25 | P3-1 | LVLNLLEL | N | n.d |
| 26 | P3-2 | VLNLLEL | N | n.d |

TABLE 6-continued

HLA-A2 binding affinities and CTL activities in the $^{51}$Cr Release Assay using T2 cells as target cells loaded with individual peptides for CTL generated with truncated versions of peptides, P3 (A), P13 (B), and P14 (C). HLA-A2 binding affinity and CTL activity were characterized as Strong (S), Median (M), Weak (W), None (N), or not determined (n.d.).

| SEQ ID NO | Peptide No. | Peptide Seq. | HLA-A2 Binding | CTL Activity |
|---|---|---|---|---|
| 27 | P3-3 | LNLLEL | N | n.d |
| 28 | P3-4 | SLVLNLLE | N | n.d |
| 29 | P3-5 | SLVLNLL | N | n.d |
| 30 | P3-6 | SLVLNL | N | n.d |
| 31 | P3-7 | SLVLNLL | N | n.d |
| 32 | P3-8 | LVLNLLE | N | M |
| B |
| 13 | P13 | TLVDLPGMTKV | M | M |
| 33 | P13-1 | LVDLPGMTKV | N | n.d |
| 34 | P13-2 | VDLPGMTKV | N | n.d |
| 35 | P13-3 | DLPGMTKV | N | n.d |
| 36 | P13-4 | LPGMTKV | N | n.d |
| 37 | P13-5 | PGMTKV | N | n.d |
| 38 | P13-6 | TLVDLPGMTK | N | n.d |
| 39 | P13-7 | TLVDLPGMT | N | n.d |
| 40 | P13-8 | TLVDLPGM | N | M |
| 41 | P13-9 | TLVDLPG | N | n.d |
| 42 | P13-10 | TLVDLP | N | S |
| 43 | P13-11 | LVDLPGMT | N | n.d |
| 44 | P13-12 | VDLPGMTK | N | n.d |
| 45 | P13-13 | LVDLPGM | M | W |
| 46 | P13-14 | VDLPGMT | N | n.d |
| 47 | P13-15 | DLPGMTK | N | n.d |
| C |
| 14 | P14 | TLIDLPGITRV | M | M |
| 48 | P14-1 | LIDLPGITRV | N | n.d |
| 49 | P14-2 | IDLPGITRV | N | n.d |
| 50 | P14-3 | DLPGITRV | N | n.d |
| 51 | P14-4 | LPGITRV | N | n.d |
| 52 | P14-5 | PGITRV | N | n.d |
| 53 | P14-6 | TLIDLPGITR | N | n.d |
| 54 | P14-7 | TLIDLPGIT | N | n.d |
| 55 | P14-8 | TLIDLPGI | N | n.d |
| 56 | P14-9 | TLIDLPG | N | n.d |
| 57 | P14-10 | TLIDLP | N | n.d |
| 58 | P14-11 | TLIDLPGIT | N | n.d |
| 59 | P14-12 | LIDLPGITR | N | n.d |
| 60 | P14-13 | LIDLPGIT | N | n.d |
| 61 | P14-14 | IDLPGITR | W | M |
| 62 | P14-15 | LIDLPGI | W | S |
| 63 | P14-16 | IDLPGIT | W | W |
| 64 | P14-17 | DLPGITR | N | n.d |

TABLE 7

HLA-A2 binding affinities and CTL activities in the $^{51}$Cr Release Assay using T2 cells as target cells loaded with computer predicted peptides derived from a search for HLA binding motifs among the full-length proteins identified original peptide sequences. HLA-A2 binding affinity and CTL activity were characterized as Strong (S), Median (M), Weak (W) None (N), or not determined (n.d.).

| SEQ ID NO | Peptide No. | Peptide Seq. | HLA-A2 Binding | CTL Activity |
|---|---|---|---|---|
| 65 | P3-9 | NLLELVHLL | S | n.d |
| 66 | P3-10 | WLTVLFIFRI | N | S |
| 67 | P3-11 | LVYLGHVIYL | W | S |
| 68 | P13-16 | KLHDAIVEVV | M | W |
| 69 | P13-17 | KLHDAIVEV | S | S |
| 70 | P13-18 | FVPEVSFEL | S | M |
| 71 | P14-18 | FMLQTYGQQL | N | n.d |
| 72 | P14-19 | FQMEQIVYC | M | M |

Figure 6A:
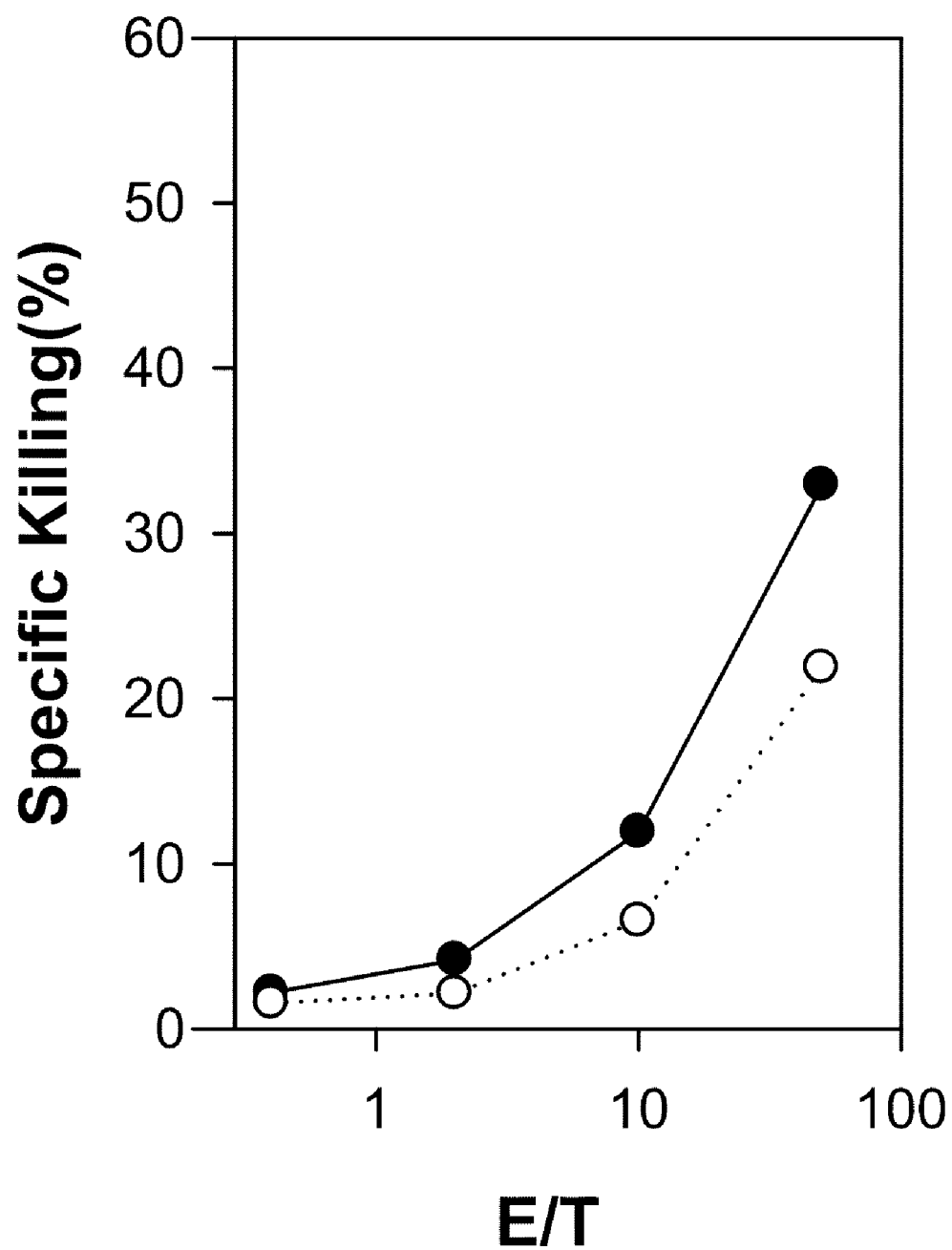
FIG. 6: Shown are graphs of CTL lysis activities against 4 different tumor cell lines with CTL generated from a single HLA-A2 positive donor (Donor 16), using a mixture of three peptides (P3, P13, and P14). The four cell lines were U266 (ATCC No. TIB-196), IFN-α treated U266, ATCC No. CCL-8083, and ATCC No. CCL-1484. Data are shown as Specific Killing (%) vs. Effector (E) Target (T) ratio (E/T). Shown in (A) are results for Specific Killing (%) of IFN-α treated U266 cells (filled circle) and U266 cells (open circles). Shown in (B) are results for Specific Killing (%) of IFN-α treated CCL-8083 cells (filled circle) and CCL-1484 cells (open circles).
Figure 6B:
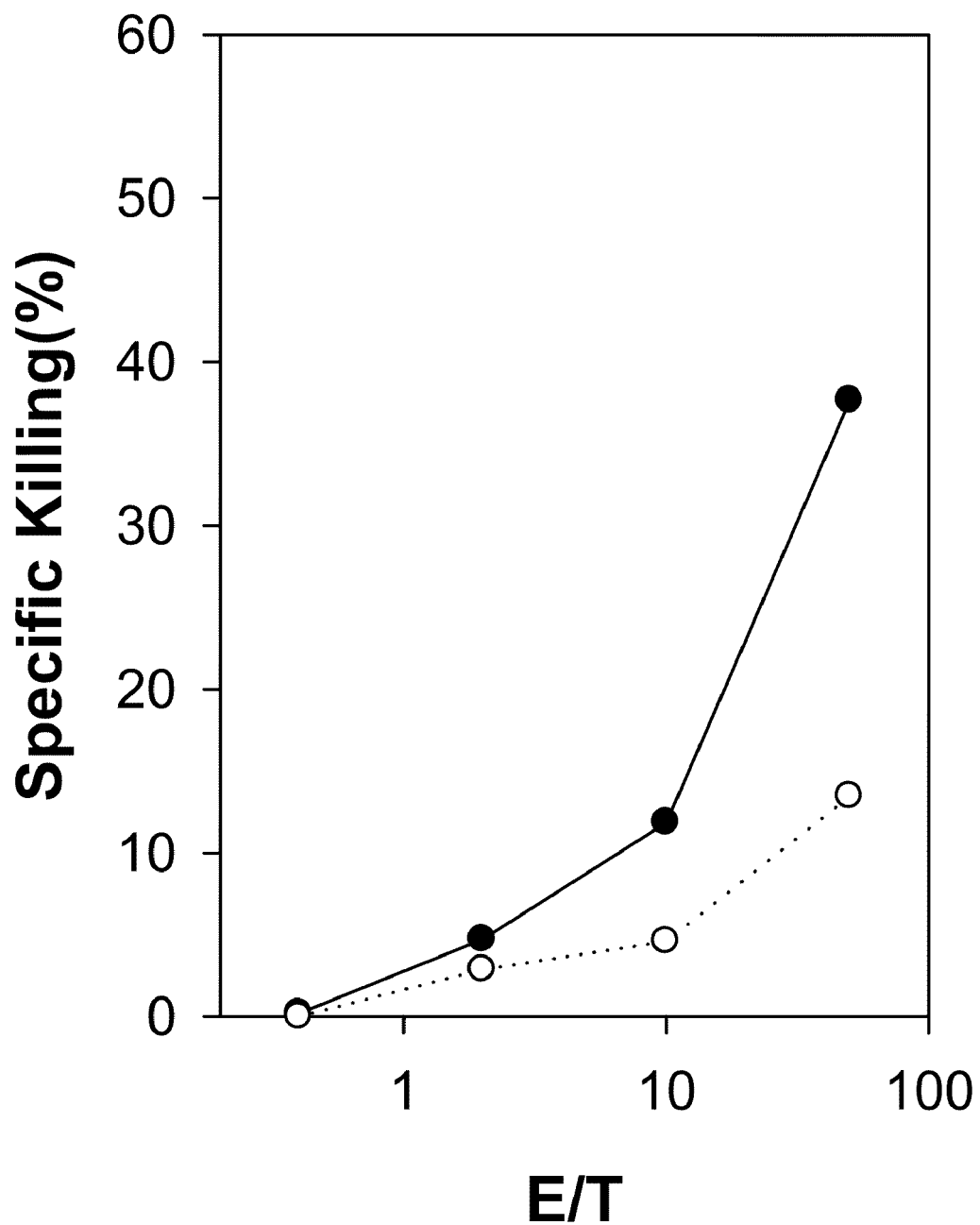

Additionally, CTL generated by the combination of three different peptides (P3, P13, and P14) were tested for their ability to kill 4 different tumor cell lines, U266 (ATCC No. TIB-196), IFN-α treated U266 ATCC No. CCL-8083, and ATCC No. CCL-1484 (FIG. 6). CTL generated from the combination of three different peptides killed cell lines U266, IFN-α treated U266, and CCL-8083, but not CCL-1484. Cell line CCL-1484 expresses MX-1 and DNML-1, but not MHC class I, which indicated that CTL killing is MHC dependant.

Western Blot of Cell Lysates

Western blots were used to quantify expression of two proteins, interferon-induced Mx protein (MX1) and Dynamin 1-like protein (DNM1L), corresponding to two identified peptides P14 and P13, respectively. Goat anti-human MX1 polyclonal antibody (Cat. No. sc-34128) and Donkey anti-Goat Ap conjugated antibody were purchased from Santa Cruz Biotechnology. Mouse anti-human DNM1L polyclonal antibody (Cat. No. NB110-55237) and anti-mouse AP conjugated antibody were from Novus Biological. Cell lysates were made from fresh cultured cells. Briefly, cells were harvested and washed 3 times with 1×PBS, cell pellets were resuspended in lysis buffer (CelLytic™ M Cell Lysis Reagent, Sigma, C2978-50, 1×10$^8$ cells/ml), and rotated at 4° C. for 1 hour. Lysates were clarified by centrifugation and protein concentration in cell lysates was measured by BCA method. 3 ug of cell lysates were run on 10-20% SDS-PAGE and transferred to nitrocellulose membrane. Anti-MX1 and anti-DNM1L antibodies were used to probe blots and detected using WesternBreeze Kit (Invitrogen, WB7104). Results of the Western blots indicated that MX1 was expressed on most tumor cells and increased in expression after treatment of cells with IFNα. No MX1 expression was detected in PBMC from normal human donors. Western blots indicated that DNM1L was expressed on all cell types.

The invention claimed is:

1. A synthetic peptide that is capable of activating T lymphocytes, wherein the synthetic peptide consisting of an amino acid sequence selected from the group consisting of: SLVLNLLEL (SEQ ID NO:3), KNPVLLKIL (SEQ ID NO:7), NLLPKLHVV (SEQ ID NO:9), FLLPHPGLQV (SEQ ID NO:10), LLNMPPAHLK (SEQ ID NO:11), TLVDLPGMTKV (SEQ ID NO:13), TLIDLPGITRV (SEQ ID NO:14), LSLDSSLSSLL (SEQ ID NO:17), LLLDVAYGAVQA (SEQ ID NO:22), FLASESLLKGAL (SEQ ID NO:23), LVLNLLE (SEQ ID NO:32), TLVDLPGM (SEQ ID NO:40), IDLPGITR (SEQ ID NO:61), WLTVLFIFRI (SEQ ID NO:66), LVYLGHVIYL (SEQ ID NO:67), FVPEVSFEL (SEQ ID NO:70), and FQMEQIVYC (SEQ ID NO:72).

2. A composition comprising at least two antigenic peptide that is capable of activating T lymphocytes, wherein the antigenic peptide consisting of an amino acid sequence selected from the group consisting of: SLVLNLLEL (SEQ ID NO:3), KNPVLLKIL (SEQ ID NO:7), NLLPKLHVV (SEQ ID NO:9), FLLPHPGLQV (SEQ ID NO:10), LLNMPPAHLK (SEQ ID NO:11), TLVDLPGMTKV (SEQ ID NO:13), TLIDLPGITRV (SEQ ID NO:14), LSLDSSLSSLL (SEQ ID NO:17), LLLDVAYGAVQA (SEQ ID NO:22), FLASESLLKGAL (SEQ ID NO:23), LVLNLLE (SEQ ID NO:32), TLVDLPGM (SEQ ID NO:40), IDLPGITR (SEQ ID NO:61), WLTVLFIFRI (SEQ ID NO:66), LVYLGHVIYL (SEQ ID NO:67), FVPEVSFEL (SEQ ID NO:70), and FQMEQIVYC (SEQ ID NO:72).

3. The composition of claim 2 in a pharmaceutically acceptable buffer.

* * * * *

```
                         SEQUENCE LISTING

<160> NUMBER OF SEQ ID NOS: 73

<210> SEQ ID NO 1
<211> LENGTH: 9
<212> TYPE: PRT
<213> ORGANISM: Homo sapiens

<400> SEQUENCE: 1

Leu Leu Gly Pro Arg Leu Val Leu Ala
1               5

<210> SEQ ID NO 2
<211> LENGTH: 9
<212> TYPE: PRT
<213> ORGANISM: Homo sapiens

<400> SEQUENCE: 2

Leu Leu Pro Gly Arg Thr Val Leu Val
1               5

<210> SEQ ID NO 3
<211> LENGTH: 9
<212> TYPE: PRT
<213> ORGANISM: Homo sapiens

<400> SEQUENCE: 3

Ser Leu Val Leu Asn Leu Leu Glu Leu
1               5

<210> SEQ ID NO 4
<211> LENGTH: 9
<212> TYPE: PRT
<213> ORGANISM: Homo sapiens

<400> SEQUENCE: 4

Arg Ser Leu Phe Leu Leu Tyr Ala Leu
1               5

<210> SEQ ID NO 5
<211> LENGTH: 9
<212> TYPE: PRT
<213> ORGANISM: Homo sapiens

<400> SEQUENCE: 5

Val Leu Ile Pro Lys Leu Pro Gln Leu
1               5

<210> SEQ ID NO 6
<211> LENGTH: 9
<212> TYPE: PRT
<213> ORGANISM: Homo sapiens
```

```
<400> SEQUENCE: 6

Lys Leu Leu Glu Pro Val Leu Leu Leu
1               5

<210> SEQ ID NO 7
<211> LENGTH: 9
<212> TYPE: PRT
<213> ORGANISM: Homo sapiens

<400> SEQUENCE: 7

Lys Asn Pro Val Leu Leu Lys Ile Leu
1               5

<210> SEQ ID NO 8
<211> LENGTH: 9
<212> TYPE: PRT
<213> ORGANISM: Homo sapiens

<400> SEQUENCE: 8

Tyr Leu Leu Pro Ala Ile Val His Ile
1               5

<210> SEQ ID NO 9
<211> LENGTH: 9
<212> TYPE: PRT
<213> ORGANISM: Homo sapiens

<400> SEQUENCE: 9

Asn Leu Leu Pro Lys Leu His Val Val
1               5

<210> SEQ ID NO 10
<211> LENGTH: 10
<212> TYPE: PRT
<213> ORGANISM: Homo sapiens

<400> SEQUENCE: 10

Phe Leu Leu Pro His Pro Gly Leu Gln Val
1               5                   10

<210> SEQ ID NO 11
<211> LENGTH: 10
<212> TYPE: PRT
<213> ORGANISM: Homo sapiens

<400> SEQUENCE: 11

Leu Leu Asn Met Pro Pro Ala His Leu Lys
1               5                   10

<210> SEQ ID NO 12
<211> LENGTH: 10
<212> TYPE: PRT
<213> ORGANISM: Homo sapiens

<400> SEQUENCE: 12

Leu Leu Tyr Gln Gly Pro His Asn Thr Leu
1               5                   10

<210> SEQ ID NO 13
<211> LENGTH: 11
<212> TYPE: PRT
<213> ORGANISM: Homo sapiens
```

```
<400> SEQUENCE: 13

Thr Leu Val Asp Leu Pro Gly Met Thr Lys Val
1               5                   10

<210> SEQ ID NO 14
<211> LENGTH: 11
<212> TYPE: PRT
<213> ORGANISM: Homo sapiens

<400> SEQUENCE: 14

Thr Leu Ile Asp Leu Pro Gly Ile Thr Arg Val
1               5                   10

<210> SEQ ID NO 15
<211> LENGTH: 11
<212> TYPE: PRT
<213> ORGANISM: Homo sapiens

<400> SEQUENCE: 15

Ala Leu Asn Glu Glu Ala Gly Arg Leu Leu Leu
1               5                   10

<210> SEQ ID NO 16
<211> LENGTH: 11
<212> TYPE: PRT
<213> ORGANISM: Homo sapiens

<400> SEQUENCE: 16

His Ser Leu Asp Asn Ser Leu Ser Ile Leu Arg
1               5                   10

<210> SEQ ID NO 17
<211> LENGTH: 11
<212> TYPE: PRT
<213> ORGANISM: Homo sapiens

<400> SEQUENCE: 17

Leu Ser Leu Asp Ser Ser Leu Ser Ser Leu Leu
1               5                   10

<210> SEQ ID NO 18
<211> LENGTH: 10
<212> TYPE: PRT
<213> ORGANISM: Homo sapiens

<400> SEQUENCE: 18

Leu Lys Asn Lys Leu Lys Asp Leu Gly His
1               5                   10

<210> SEQ ID NO 19
<211> LENGTH: 12
<212> TYPE: PRT
<213> ORGANISM: Homo sapiens

<400> SEQUENCE: 19

Asn Leu Lys Ala Ala Leu Glu Asn Leu Gly Ala Leu
1               5                   10

<210> SEQ ID NO 20
<211> LENGTH: 11
<212> TYPE: PRT
<213> ORGANISM: Homo sapiens
```

```
<400> SEQUENCE: 20

Leu Leu Ile Asp Asp Lys Gly Thr Ile Lys Leu
1               5                   10

<210> SEQ ID NO 21
<211> LENGTH: 12
<212> TYPE: PRT
<213> ORGANISM: Homo sapiens

<400> SEQUENCE: 21

Leu Leu Leu Asp Val Pro Thr Ala Ala Val Gln Ala
1               5                   10

<210> SEQ ID NO 22
<211> LENGTH: 12
<212> TYPE: PRT
<213> ORGANISM: Homo sapiens

<400> SEQUENCE: 22

Leu Leu Leu Asp Val Ala Tyr Gly Ala Val Gln Ala
1               5                   10

<210> SEQ ID NO 23
<211> LENGTH: 12
<212> TYPE: PRT
<213> ORGANISM: Homo sapiens

<400> SEQUENCE: 23

Phe Leu Ala Ser Glu Ser Leu Leu Lys Gly Ala Leu
1               5                   10

<210> SEQ ID NO 24
<211> LENGTH: 10
<212> TYPE: PRT
<213> ORGANISM: Homo sapiens

<400> SEQUENCE: 24

Leu Lys Ile His Ala Arg Glu Ile Phe Asp
1               5                   10

<210> SEQ ID NO 25
<211> LENGTH: 8
<212> TYPE: PRT
<213> ORGANISM: Homo sapiens

<400> SEQUENCE: 25

Leu Val Leu Asn Leu Leu Glu Leu
1               5

<210> SEQ ID NO 26
<211> LENGTH: 7
<212> TYPE: PRT
<213> ORGANISM: Homo sapiens

<400> SEQUENCE: 26

Val Leu Asn Leu Leu Glu Leu
1               5

<210> SEQ ID NO 27
<211> LENGTH: 6
<212> TYPE: PRT
<213> ORGANISM: Homo sapiens
```

```
<400> SEQUENCE: 27

Leu Asn Leu Leu Glu Leu
1               5

<210> SEQ ID NO 28
<211> LENGTH: 8
<212> TYPE: PRT
<213> ORGANISM: Homo sapiens

<400> SEQUENCE: 28

Ser Leu Val Leu Asn Leu Leu Glu
1               5

<210> SEQ ID NO 29
<211> LENGTH: 7
<212> TYPE: PRT
<213> ORGANISM: Homo sapiens

<400> SEQUENCE: 29

Ser Leu Val Leu Asn Leu Leu
1               5

<210> SEQ ID NO 30
<211> LENGTH: 6
<212> TYPE: PRT
<213> ORGANISM: Homo sapiens

<400> SEQUENCE: 30

Ser Leu Val Leu Asn Leu
1               5

<210> SEQ ID NO 31
<211> LENGTH: 7
<212> TYPE: PRT
<213> ORGANISM: Homo sapiens

<400> SEQUENCE: 31

Ser Leu Val Leu Asn Leu Leu
1               5

<210> SEQ ID NO 32
<211> LENGTH: 7
<212> TYPE: PRT
<213> ORGANISM: Homo sapiens

<400> SEQUENCE: 32

Leu Val Leu Asn Leu Leu Glu
1               5

<210> SEQ ID NO 33
<211> LENGTH: 10
<212> TYPE: PRT
<213> ORGANISM: Homo sapiens

<400> SEQUENCE: 33

Leu Val Asp Leu Pro Gly Met Thr Lys Val
1               5                   10

<210> SEQ ID NO 34
<211> LENGTH: 9
<212> TYPE: PRT
<213> ORGANISM: Homo sapiens
```

```
<400> SEQUENCE: 34

Val Asp Leu Pro Gly Met Thr Lys Val
1               5

<210> SEQ ID NO 35
<211> LENGTH: 8
<212> TYPE: PRT
<213> ORGANISM: Homo sapiens

<400> SEQUENCE: 35

Asp Leu Pro Gly Met Thr Lys Val
1               5

<210> SEQ ID NO 36
<211> LENGTH: 7
<212> TYPE: PRT
<213> ORGANISM: Homo sapiens

<400> SEQUENCE: 36

Leu Pro Gly Met Thr Lys Val
1               5

<210> SEQ ID NO 37
<211> LENGTH: 6
<212> TYPE: PRT
<213> ORGANISM: Homo sapiens

<400> SEQUENCE: 37

Pro Gly Met Thr Lys Val
1               5

<210> SEQ ID NO 38
<211> LENGTH: 10
<212> TYPE: PRT
<213> ORGANISM: Homo sapiens

<400> SEQUENCE: 38

Thr Leu Val Asp Leu Pro Gly Met Thr Lys
1               5                   10

<210> SEQ ID NO 39
<211> LENGTH: 9
<212> TYPE: PRT
<213> ORGANISM: Homo sapiens

<400> SEQUENCE: 39

Thr Leu Val Asp Leu Pro Gly Met Thr
1               5

<210> SEQ ID NO 40
<211> LENGTH: 8
<212> TYPE: PRT
<213> ORGANISM: Homo sapiens

<400> SEQUENCE: 40

Thr Leu Val Asp Leu Pro Gly Met
1               5

<210> SEQ ID NO 41
<211> LENGTH: 7
<212> TYPE: PRT
<213> ORGANISM: Homo sapiens
```

```
<400> SEQUENCE: 41

Thr Leu Val Asp Leu Pro Gly
1               5

<210> SEQ ID NO 42
<211> LENGTH: 6
<212> TYPE: PRT
<213> ORGANISM: Homo sapiens

<400> SEQUENCE: 42

Thr Leu Val Asp Leu Pro
1               5

<210> SEQ ID NO 43
<211> LENGTH: 8
<212> TYPE: PRT
<213> ORGANISM: Homo sapiens

<400> SEQUENCE: 43

Leu Val Asp Leu Pro Gly Met Thr
1               5

<210> SEQ ID NO 44
<211> LENGTH: 8
<212> TYPE: PRT
<213> ORGANISM: Homo sapiens

<400> SEQUENCE: 44

Val Asp Leu Pro Gly Met Thr Lys
1               5

<210> SEQ ID NO 45
<211> LENGTH: 7
<212> TYPE: PRT
<213> ORGANISM: Homo sapiens

<400> SEQUENCE: 45

Leu Val Asp Leu Pro Gly Met
1               5

<210> SEQ ID NO 46
<211> LENGTH: 7
<212> TYPE: PRT
<213> ORGANISM: Homo sapiens

<400> SEQUENCE: 46

Val Asp Leu Pro Gly Met Thr
1               5

<210> SEQ ID NO 47
<211> LENGTH: 7
<212> TYPE: PRT
<213> ORGANISM: Homo sapiens

<400> SEQUENCE: 47

Asp Leu Pro Gly Met Thr Lys
1               5

<210> SEQ ID NO 48
<211> LENGTH: 10
<212> TYPE: PRT
<213> ORGANISM: Homo sapiens
```

<400> SEQUENCE: 48

Leu Ile Asp Leu Pro Gly Ile Thr Arg Val
1               5                   10

<210> SEQ ID NO 49
<211> LENGTH: 9
<212> TYPE: PRT
<213> ORGANISM: Homo sapiens

<400> SEQUENCE: 49

Ile Asp Leu Pro Gly Ile Thr Arg Val
1               5

<210> SEQ ID NO 50
<211> LENGTH: 8
<212> TYPE: PRT
<213> ORGANISM: Homo sapiens

<400> SEQUENCE: 50

Asp Leu Pro Gly Ile Thr Arg Val
1               5

<210> SEQ ID NO 51
<211> LENGTH: 7
<212> TYPE: PRT
<213> ORGANISM: Homo sapiens

<400> SEQUENCE: 51

Leu Pro Gly Ile Thr Arg Val
1               5

<210> SEQ ID NO 52
<211> LENGTH: 6
<212> TYPE: PRT
<213> ORGANISM: Homo sapiens

<400> SEQUENCE: 52

Pro Gly Ile Thr Arg Val
1               5

<210> SEQ ID NO 53
<211> LENGTH: 10
<212> TYPE: PRT
<213> ORGANISM: Homo sapiens

<400> SEQUENCE: 53

Thr Leu Ile Asp Leu Pro Gly Ile Thr Arg
1               5                   10

<210> SEQ ID NO 54
<211> LENGTH: 9
<212> TYPE: PRT
<213> ORGANISM: Homo sapiens

<400> SEQUENCE: 54

Thr Leu Ile Asp Leu Pro Gly Ile Thr
1               5

<210> SEQ ID NO 55
<211> LENGTH: 8
<212> TYPE: PRT
<213> ORGANISM: Homo sapiens

```
<400> SEQUENCE: 55

Thr Leu Ile Asp Leu Pro Gly Ile
1               5

<210> SEQ ID NO 56
<211> LENGTH: 7
<212> TYPE: PRT
<213> ORGANISM: Homo sapiens

<400> SEQUENCE: 56

Thr Leu Ile Asp Leu Pro Gly
1               5

<210> SEQ ID NO 57
<211> LENGTH: 6
<212> TYPE: PRT
<213> ORGANISM: Homo sapiens

<400> SEQUENCE: 57

Thr Leu Ile Asp Leu Pro
1               5

<210> SEQ ID NO 58
<211> LENGTH: 9
<212> TYPE: PRT
<213> ORGANISM: Homo sapiens

<400> SEQUENCE: 58

Thr Leu Ile Asp Leu Pro Gly Ile Thr
1               5

<210> SEQ ID NO 59
<211> LENGTH: 9
<212> TYPE: PRT
<213> ORGANISM: Homo sapiens

<400> SEQUENCE: 59

Leu Ile Asp Leu Pro Gly Ile Thr Arg
1               5

<210> SEQ ID NO 60
<211> LENGTH: 8
<212> TYPE: PRT
<213> ORGANISM: Homo sapiens

<400> SEQUENCE: 60

Leu Ile Asp Leu Pro Gly Ile Thr
1               5

<210> SEQ ID NO 61
<211> LENGTH: 8
<212> TYPE: PRT
<213> ORGANISM: Homo sapiens

<400> SEQUENCE: 61

Ile Asp Leu Pro Gly Ile Thr Arg
1               5

<210> SEQ ID NO 62
<211> LENGTH: 7
<212> TYPE: PRT
<213> ORGANISM: Homo sapiens
```

-continued

```
<400> SEQUENCE: 62

Leu Ile Asp Leu Pro Gly Ile
1               5

<210> SEQ ID NO 63
<211> LENGTH: 7
<212> TYPE: PRT
<213> ORGANISM: Homo sapiens

<400> SEQUENCE: 63

Ile Asp Leu Pro Gly Ile Thr
1               5

<210> SEQ ID NO 64
<211> LENGTH: 7
<212> TYPE: PRT
<213> ORGANISM: Homo sapiens

<400> SEQUENCE: 64

Asp Leu Pro Gly Ile Thr Arg
1               5

<210> SEQ ID NO 65
<211> LENGTH: 9
<212> TYPE: PRT
<213> ORGANISM: Homo sapiens

<400> SEQUENCE: 65

Asn Leu Leu Glu Leu Val His Leu Leu
1               5

<210> SEQ ID NO 66
<211> LENGTH: 10
<212> TYPE: PRT
<213> ORGANISM: Homo sapiens

<400> SEQUENCE: 66

Trp Leu Thr Val Leu Phe Ile Phe Arg Ile
1               5                   10

<210> SEQ ID NO 67
<211> LENGTH: 10
<212> TYPE: PRT
<213> ORGANISM: Homo sapiens

<400> SEQUENCE: 67

Leu Val Tyr Leu Gly His Val Ile Tyr Leu
1               5                   10

<210> SEQ ID NO 68
<211> LENGTH: 10
<212> TYPE: PRT
<213> ORGANISM: Homo sapiens

<400> SEQUENCE: 68

Lys Leu His Asp Ala Ile Val Glu Val Val
1               5                   10

<210> SEQ ID NO 69
<211> LENGTH: 9
<212> TYPE: PRT
<213> ORGANISM: Homo sapiens
```

-continued

```
<400> SEQUENCE: 69

Lys Leu His Asp Ala Ile Val Glu Val
1               5

<210> SEQ ID NO 70
<211> LENGTH: 9
<212> TYPE: PRT
<213> ORGANISM: Homo sapiens

<400> SEQUENCE: 70

Phe Val Pro Glu Val Ser Phe Glu Leu
1               5

<210> SEQ ID NO 71
<211> LENGTH: 10
<212> TYPE: PRT
<213> ORGANISM: Homo sapiens

<400> SEQUENCE: 71

Phe Met Leu Gln Thr Tyr Gly Gln Gln Leu
1               5                   10

<210> SEQ ID NO 72
<211> LENGTH: 9
<212> TYPE: PRT
<213> ORGANISM: Homo sapiens

<400> SEQUENCE: 72

Phe Gln Met Glu Gln Ile Val Tyr Cys
1               5

<210> SEQ ID NO 73
<211> LENGTH: 10
<212> TYPE: PRT
<213> ORGANISM: Hepatitis B Virus

<400> SEQUENCE: 73

Phe Leu Pro Ser Asp Phe Phe Pro Ser Val
1               5                   10
```